(12) United States Patent
Storey et al.

(10) Patent No.: US 7,767,796 B2
(45) Date of Patent: Aug. 3, 2010

(54) N4 CHELATOR CONJUGATES

(75) Inventors: Anthony Eamonn Storey, Amersham (GB); Harry John Wadsworth, Amersham (GB); Nigel Anthony Powell, Amersham (GB); Philip Duncanson, London (GB)

(73) Assignee: GE Healthcare Limited, Buckinghamshire (GB)

( * ) Notice: Subject to any disclaimer, the term of this patent is extended or adjusted under 35 U.S.C. 154(b) by 285 days.

(21) Appl. No.: 11/572,161

(22) PCT Filed: Jul. 19, 2005

(86) PCT No.: PCT/GB2005/002807

§ 371 (c)(1),
(2), (4) Date: Sep. 10, 2007

(87) PCT Pub. No.: WO2006/008496

PCT Pub. Date: Jan. 26, 2006

(65) Prior Publication Data

US 2008/0131368 A1    Jun. 5, 2008

(30) Foreign Application Priority Data

Jul. 19, 2004    (GB) ................................ 0416062.8

(51) Int. Cl.
*C07F 13/00* (2006.01)

(52) U.S. Cl. .................. 534/14; 424/1.11; 424/1.65; 534/10

(58) Field of Classification Search ................ 424/1.11, 424/1.37, 1.65, 1.49, 1.69, 9.1, 9.3, 9.4, 9.5; 534/7, 10–14

See application file for complete search history.

(56) References Cited

U.S. PATENT DOCUMENTS

| 5,053,493 | A | * | 10/1991 | Pak et al. .................. 530/391.5 |
| 5,175,343 | A | * | 12/1992 | Fritzberg et al. ............. 560/145 |
| 5,242,679 | A | * | 9/1993 | Fritzberg et al. ............ 424/1.53 |
| 5,489,425 | A | * | 2/1996 | Kruper et al. ............... 424/1.11 |

FOREIGN PATENT DOCUMENTS

| EP | 0296522 | 12/1988 |
| WO | 03/006070 | 1/2003 |
| WO | 03/006491 | 1/2003 |
| WO | 03/051859 | 6/2003 |

OTHER PUBLICATIONS

Maina et al (2002), European Journal of Nuclear Medicine, vol. 29, No. 6, pp. 742-753.*
Heppeler et al (2000), Current Medicinal Chemistry, vol. 7, No. 9, pp. 971-994.*
Maina et al (European Journal of Nuclear Medicine, 2002, vol. 29, No. 6, pp. 742-753).*
Heppeler et al (Current Medicinal Chemistry, 2000, vol. 7, No. 9, pp. 971-994).*
GB0416062.8 Search Report dated Nov. 2004.
PCT/2005/002807 ISR & Written Opinion Dated Jun. 2006.
PCT/2005/002807 IPER Dated Nov. 2006.
Turpin, et.al., "Synthesis of two novel oxocyclam-binding technetium complexes containing an analogue of cocaine" Journal of labeled compounds and radiopharmaceuticals, 2002: 45: pp. 379-393.
Riche, et.al. "Nitroimidazoles and hypoxia imaging: synthesis of three technetium-99m complexes bearing a nitroimidazole group: biological results" Bioorganic & medicinal chemistry letters 11 (2001) pp. 71-74.
Lee, et.al., "Synthesis of anion receptor grafted siloxane polymers and the ionic conductivity studies of polymer-salt complexes" Journal of the electrochemical society, 146 (3) (1999) pp. 941-946.
Heppeler, A, et.al., "Receptor targeting for tumor localization and therapy with radiopeptides" Current medicinal chemistry, Bentham Science Publishers BV, BE, vol. 7, No. 9, 2000, pp. 971-994.
Maina, et.al., "[99mTc]demotate, a new 99mTc-based [Tyr3]octreotate analogue for the detection of somatostatin receptor-positive tumours: synthesis and preclinical results" European journal of nuclear medicine and molecular imaging, Jun. 2002, vol. 29, No. 6 pp. 742-753.

* cited by examiner

*Primary Examiner*—D L Jones
(74) *Attorney, Agent, or Firm*—Craig Bohlken

(57) ABSTRACT

The present invention provides tetra-amine chelator conjugates with biological targeting moieties, linked via a linker group and technetium complexes thereof as radiopharmaceuticals. The linker group is such that the chelator is mono-functionalized at the bridgehead position and provides both flexibility and a lack or aryl groups, to minimize lipophilicity and steric hulk. Protected versions of the chelators are provided which permit conjugation with a wide range of targeting molecules without interfering reactions with the amine nitrogens of the tetra-amine chelator. Syntheses of the functionalised chelators are described, together with bifunctional chelate precursors. Radiopharmaceutical compositions comprising the technetium metal complexes of the invention are described, together with non-radioactive kits for the preparation of such radiopharmaceuticals.

21 Claims, 3 Drawing Sheets

| $Q^1$ to $Q^6$ | n | E | Compound Number |
|---|---|---|---|
| $Q^1 = Q^3 = Q^4 = Q^5 = -CO_2C(CH_3)_3$<br>$Q^2 = Q^6 = H$ | 1 | $-CO_2H$ | 1 |
| $Q^1 = Q^3 = Q^4 = Q^5 = -CO_2C(CH_3)_3$<br>$Q^2 = Q^6 = H$ | 6 | $-NH_2$ | 2 |
| $Q^1 = Q^3 = Q^4 = Q^5 = -CO_2C(CH_3)_3$<br>$Q^2 = Q^6 = H$ | 1 | $-CO_2(NHS)$ | 9 |

Where NHS = N-hydroxysuccinimide active ester

| R' | Compound |
|---|---|
| -CH₂C₆H₅ | 3 |
| [structure with biphenyl-tetrazole, chloro-butyl-imidazole, and leucine amide] | 4 |
| [structure with PEG linker, glycolate, leucine, chloro-butyl-imidazole, biphenyl-tetrazole] | 5 |
| [peptide structure: ethylene-Gly-Arg-Val-Tyr-Ile-His-Pro-Ile-OH] | 8 |

| R" | Compound Number |
|---|---|
| -COC$_6$H$_5$ | 6 |
|  | 7 |

N4 CHELATOR CONJUGATES

This application is a filing under 35 U.S.C. 371 of international application number PCT/GB2005/002807, filed Jul. 19, 2005, which claims priority to application number 0416062.8 filed Jul. 19, 2004, in Great Britain the entire disclosure of which is hereby incorporated by reference.

FIELD OF THE INVENTION

The present invention relates to improved conjugates of tetra-amine chelators with biological targeting molecules, suitable for forming metal complexes with the radiometal $^{99m}$Tc. The radiometal complexes are useful as $^{99m}$Tc radiopharmaceuticals. Kits and precursors are also provided.

BACKGROUND OF THE INVENTION

U.S. Pat. No. 5,489,425 (Dow Chemical) discloses a range of open-chain and macrocyclic functionalised tetra-amine chelators useful for the complexation of metals, in particular radioactive and non-radioactive rhodium complexes, especially $^{105}$Rh or $^{101m}$Rh radiometal complexes. Specific tetramines disclosed include:

| [Linker] | Compound |
|---|---|
| —CH$_2$[p-phenylene]— | BA-2,3,2-tet |
| -[p-phenylene]- | AN-2,3,2-tet |
| —(CH$_2$)$_3$— | PA-2,3,2-tet |

The bifunctional chelators are described as useful for conjugation with monoclonal antibodies, or fragments thereof, for therapeutic or diagnostic purposes. U.S. Pat. No. 5,489,425 discloses (Examples 21, 22a and 23) that the antibody-radiometal complex chelator conjugate is prepared by first forming the $^{105}$Rh metal complex, then reaction with the antibody followed by purification. U.S. Pat. No. 5,489,425 is silent on antibody-chelator conjugates which are uncomplexed, ie. without a coordinated radiometal. U.S. Pat. No. 5,489,425 does not teach how to differentiate the pendant amine from the four amines of the chelator in such antibody conjugation reactions. U.S. Pat. No. 5,489,425 states that the bifunctional chelators "would also be useful in complexing technetium and rhenium", but does not disclose how this would be achieved or any actual technetium complexes.

U.S. Pat. No. 5,650,134 discloses somatostatin peptide-chelator conjugate of a range of chelators. Example 1 describes the conjugation to a 6-(p-isothiocyanatobenzyl)-1,4,8,11-tetraazaundecane to an octreotide peptide.

EP 1181936 A1 discloses bombesin (ie. tetradecapeptide) conjugates of tetra-amine chelators, prepared using the bifunctional chelators BBN-1 and BBN-2, and the $^{99m}$Tc complexes thereof:

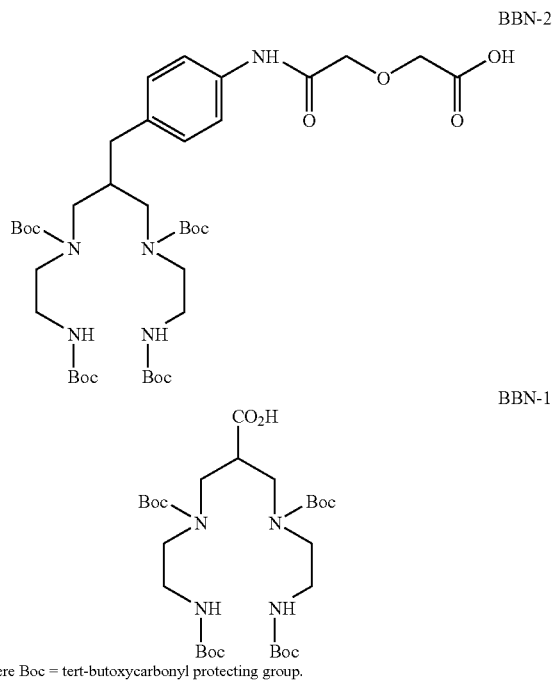

where Boc = tert-butoxycarbonyl protecting group.

The $^{99m}$Tc complexes are said to exhibit rapid clearance from the murine body via the kidneys and urinary system. EP 1181936 A1 does not, however, provide any disclosure or reference to the synthesis of BBN-1 or BBN-2, only to the step where they are conjugated to the N-terminus of bombesin. The conjugation of BBN-2 to bombesin and $^{99m}$Tc labelling to give a potential tumour imaging radiopharmaceutical has also been described by Nock et al [Eur. J. Nucl. Med., 30(2), 247-258 (2003)]. The $^{99m}$Tc complex is said to impart improved hydrophilicity compared to prior art bombesin-chelate conjugates, and hence be expected to favour excretion via the kidneys and urinary system.

The conjugation of BBN-1 to octreotide and $^{99m}$Tc labelling to give a potential tumour imaging radiopharmaceutical has been described by Maina et al for human patients [Eur. J. Nucl. Med., 30(9), 1211-1219 (2003)]. Neither of the above BBN-1 or BBN-2 publications provide any synthesis of BBN-1 or BBN-2.

THE PRESENT INVENTION

The present invention provides tetra-amine chelator conjugates with biological targeting moieties, linked via a linker group and technetium complexes thereof as radiopharmaceuticals. The linker group is such that the chelator is mono-functionalised at the bridgehead position and provides both flexibility and a lack or aryl groups, to minimise lipophilicity and steric bulk. Suitably protected versions of the chelators are provided, which permit conjugation with a wide range of targeting molecules without interfering reactions with the amine nitrogens of the tetra-amine chelator. Syntheses of the functionalised chelators are described, together with bifunctional chelate precursors.

Radiopharmaceutical compositions comprising the technetium metal complexes of the invention are described, together with non-radioactive kits for the preparation of such radiopharmaceuticals.

DETAILED DESCRIPTION OF THE INVENTION

Figure 1:
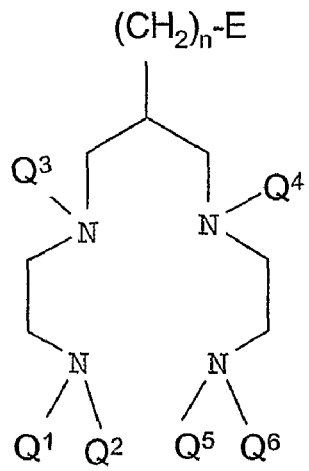
FIGS. 1, 2, and 3 disclose conjugates of tetra-amine chelators that are suitable for forming metal complexes with the radiometal $^{99m}$Tc.
Figure 2:
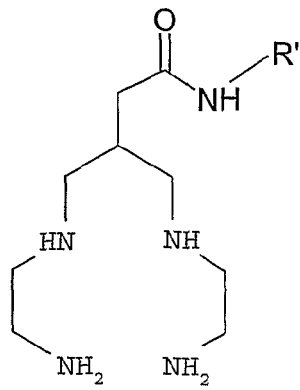
Figure 3:
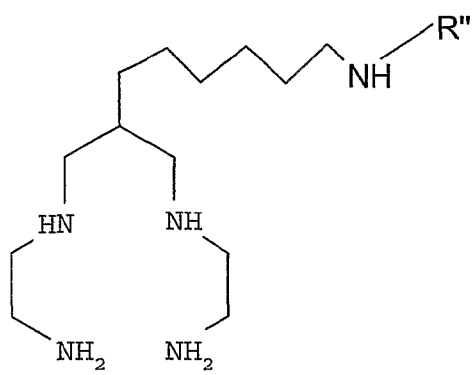

In a first embodiment, the present invention provides a cationic $^{99m}$Tc technetium complex of Formula (I):

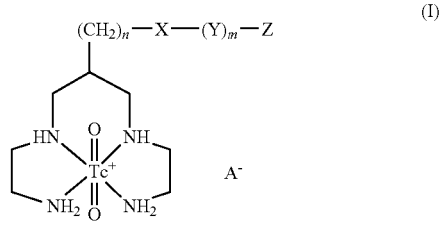

(I)

where:
X is —NR—, —CO$_2$—, —CO—, —NR(C=S)—, —NR(C=O)—, —CONR— or a Q group;
each Y is independently a D- or L-amino acid, —CH$_2$—, —CH$_2$OCH$_2$— or —OCH$_2$CH$_2$O— or an X group;
Z is a synthetic biological targeting moiety;
n is an integer of value 1 to 8;
m is an integer of value 0 to 30;
R is H, C$_{1-4}$ alkyl, C$_{2-4}$ alkoxyalkyl, C$_{1-4}$ hydroxyalkyl, or C$_{1-4}$ fluoroalkyl;
Q is

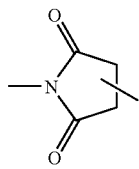

A is a counterion;
with the proviso that the X$^1$—(Y)$_m$ chain of atoms lacks bonds in which one heteroatom is directly bonded to another.

The technetium radioisotope may be a γ-emitter, such as $^{99m}$Tc or a positron emitter suitable for PET imaging such as $^{94m}$Tc. Preferably the technetium radioisotope is $^{99m}$Tc or $^{94m}$Tc, most preferably it is $^{99m}$Tc.

X is preferably —CONR—, —NR(C=O)— or a Q group. X is most preferably —CONR— or —NR(C=O)—, with —CONH— and —NH(C=O)— being especially preferred.

The linker group —(CH$_2$)$_n$—X—(Y)$_m$— of Formula I is chosen such that the X$^1$—(Y)m chain of atoms lacks bonds in which one heteroatom is directly bonded to another, where the term "heteroatom" means a non-carbon atom such as nitrogen, oxygen or sulfur. This means that the chain lacks bonds such as O—O, N—N or O—N.

It is envisaged that the role of the linker group —(CH$_2$)$_n$—X—(Y)$_m$— of Formula I is to distance the technetium complex from the active binding site of the biological targeting moiety (Z) in vivo. This helps ensure that the relatively bulky technetium complex does not sterically inhibit binding to active sites in vivo. The alkylene group —(CH$_2$)$_n$— has the advantage that there are no significant hydrogen bonding interactions with the conjugated biological targeting moiety (Z), so that the linker does not wrap round onto Z. Preferred alkylene groups have n=1 to 6, most preferably 2 to 4, with 2 being especially preferred.

The linker groups of the present invention lack aryl rings. This helps minimise the lipophilicity of the technetium complex plus linker group which is attached to the biological targeting moiety (Z) of the conjugate. The steric bulk and molecular weight of the linker group (and hence technetium complex) is also minimised, whilst flexibility of the linkage is maintained.

The nature of the linker group can also be used to modify the biodistribution of the imaging agent. Thus, eg. the introduction of ether groups in —(Y)$_m$— will help to minimise plasma protein binding. When —(Y)$_m$— comprises a polyethyleneglycol (PEG) building block or a peptide chain of 1 to 10 amino acid residues, the linker group may function to modify the pharmacokinetics and blood clearance rates of the imaging agent in vivo. Such "biomodifier" linker groups may accelerate the clearance of the technetium imaging agent from background tissue, such as muscle or liver, and/or from the blood, thus giving a better diagnostic image due to less background interference. A biomodifier linker group may also be used to favour a particular route of excretion, eg. via the kidneys as opposed to via the liver. Alternatively, they may prolong the blood residence time, allowing more agent to accumulate at the target site in vivo.

When —(Y)$_m$— comprises a peptide chain of amino acid residues, the amino acid residues are preferably chosen from glycine, lysine, aspartic acid, glutamic acid or serine. The number of amino acids in the peptide chain is preferably 1 to 10, most preferably 1 to 3.

When —(Y)$_m$— comprises a PEG moiety, it preferably comprises a group of formula (—OCH$_2$CH$_2$O—)$_w$ where w is an integer of value 3 to 25. The integer w is preferably 6 to 22. An especially preferred PEG-containing —(Y)$_m$— group is a unit derived from polymerisation of the monodisperse PEG-like structure, 17-amino-5-oxo-6-aza-3, 9, 12, 15-tetraoxaheptadecanoic acid of Formula IV:

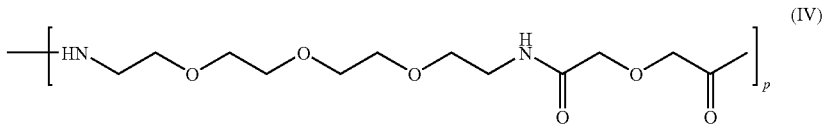

(IV)

wherein p is an integer from 1 to 10.

By the term 'fluoroalkyl' is meant an alkyl group with at least one fluorine substituent, ie. the term encompasses groups from monofluoroalkyl (eg. —CH$_2$F) to perfluoroalkyl (eg. CF$_3$).

The —(Y)$_m$— group preferably comprises a diglycolic acid moiety, a maleimide moiety, a glutaric acid, succinic acid, a polyethyleneglycol based unit or a PEG-like unit of Formula IV.

By the term "synthetic" is meant the conventional meaning of the term ie. man-made as opposed to being isolated from natural sources eg. from the mammalian body. Such compounds have the advantage that their manufacture and impurity profile can be fully controlled. Monoclonal antibodies and fragments thereof are therefore outside the scope of the present claims.

By the term "biological targeting moiety" is meant: 3-100 mer peptides or peptide analogues which may be linear peptides or cyclic peptides or combinations thereof; or enzyme substrates, antagonists or inhibitors; synthetic receptor-binding compounds; oligonucleotides, or oligo-DNA or oligo-RNA fragments.

By the term "cyclic peptide" is meant a sequence of 5 to 15 amino acids in which the two terminal amino acids are bonded together by a covalent bond which may be a peptide or disulphide bond or a synthetic non-peptide bond such as a thioether, phosphodiester, disiloxane or urethane bond. By the term "amino acid" is meant an L- or D-amino acid, amino acid analogue or amino acid mimetic which may be optically pure, i.e. a single enantiomer and hence chiral, or a mixture of enantiomers. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)].

Suitable peptides for use in the present invention include:
somatostatin, octreotide and analogues,
peptides which bind to the ST receptor, where ST refers to the heat-stable toxin produced by *E. coli* and other micro-organisms;
laminin fragments eg. YIGSR, PDSGR, IKVAV, LRE and KCQAGTFALRGDPQG,
N-formyl peptides for targeting sites of leucocyte accumulation,
Platelet factor 4 (PF4) and fragments thereof,
RGD (Arg-Gly-Asp)-containing peptides, which may eg. target angiogenesis [R. Pasqualini et al., Nat Biotechnol. 1997 Jun; 15(6):542-6]; [E. Ruoslahti, Kidney Int. 1997 May; 51(5):1413-7].
peptide fragments of α$_2$-antiplasmin, fibronectin or beta-casein, fibrinogen or thrombospondin. The amino acid sequences of α$_2$-antiplasmin, fibronectin, beta-casein, fibrinogen and thrombospondin can be found in the following references: α$_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984);
peptides which are substrates or inhibitors of angiotensin, such as:
angiotensin II Asp-Arg-Val-Tyr-Ile-His-Pro- Phe (E. C. Jorgensen et al, *J. Med. Chem.*, 1979, Vol 22, 9, 1038-1044)
[Sar, Ile] Angiotensin II: Sar-Arg-Val-Tyr-Ile-His-Pro-Ile (R. K. Turker et al., *Science*, 1972, 177, 1203).
Angiotensin I: Asp-Arg-Val-Tyr-Ile-His-Pro- Phe-His-Leu.

Preferably the peptides of the present invention comprise antiplasmin or angiotensin II peptides. Antiplasmin peptides comprise an amino acid sequence taken from the N-terminus of:
(i) α$_2$-antiplasmin,
i.e. NH$_2$-Asn-Gln-Glu-Gln-Val-Ser-Pro-Leu-Thr-Leu-Thr-Leu-Leu-Lys-OH or variants of this in which one or more amino acids have been exchanged, added or removed such as:
NH$_2$-Asn-Gln-Glu-Gln-Val-Ser-Pro-Leu-Thr-Leu-Thr-Leu-Leu-Lys-Gly-OH,
NH$_2$-Asn-Gln-Glu-Ala-Val-Ser-Pro-Leu-Thr-Leu-Thr-Leu-Leu-Lys-Gly-OH,
NH$_2$-Asn-Gln-Glu-Gln-Val-Gly-OH; or
(ii) casein
ie. Ac-Leu-Gly-Pro-Gly-Gln-Ser-Lys-Val-Ile-Gly.

Synthetic peptides of the present invention may be obtained by conventional solid phase synthesis, as described in P. Lloyd-Williams, F. Albericio and E. Girald; *Chemical Approaches to the Synthesis of Peptides and Proteins*, CRC Press, 1997.

Suitable enzyme substrates, antagonists or inhibitors include glucose and glucose analogues such as fluorodeoxyglucose; fatty acids, or elastase, Angiotensin II or metalloproteinase inhibitors. A preferred non-peptide Angiotensin II antagonist is Losartan.

Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor.

The biological targeting moiety (Z) is preferably of molecular weight of less than 5000, most preferably less than 4000, ideally less than 3000. This has the advantage that the improved biological characteristics of the tetra-amine technetium complexes of the invention can have an influence on the overall biodistribution, particularly the clearance, of the technetium complex of the conjugate of Formula I. When n is 3, and X comprises a nitrogen atom directly bonded to the (CH$_2$)$_n$ group, then Z is chosen to be both synthetic and having a molecular weight of less than 4000. Preferred biological targeting moieties are 3-20 mer peptides or enzyme substrates, enzyme antagonists or enzyme inhibitors.

The counterion (A$^-$) represents an anion which is present in a molar equivalent amount, thus balancing the positive charge on the Tc(V) dioxo technetium complex of Formula I. The anion (A) is suitably singly- or multiply-charged, as long as a charge-balancing amount is present. The anion is suitably derived from an inorganic or organic acid. Examples of suitable anions include: halide ions such as chloride or bromide, sulphate, nitrate, citrate, acetate, phosphate and borate. Preferred anions are chloride.

The technetium complexes of Formula I have the advantage that they are stable after complex formation, and comprise an avid cheland which binds technetium preferentially to the biological targeting moiety. The technetium complex is consequently unlikely to undergo transchelation reactions with biological macromolecules or competing ligands in vivo. The technetium complexes are small and compact which is useful in having minimal steric impact on the conjugated biological targeting moiety (Z). The permanent cationic change and the Tc(V) dioxo core means that the complexes are also hydrophilic, and hence unlikely to be distributed intracellularly into other compartments, with consequently more rapid clearance from background organs and tissues in vivo, eg. from the bloodstream.

The technetium complexes of Formula I may be prepared by reaction of a suitable source of technetium with a chelator conjugate of Formula II, as described in the second embodiment below.

In a second embodiment, the present invention provides a chelator conjugate of Formula II:

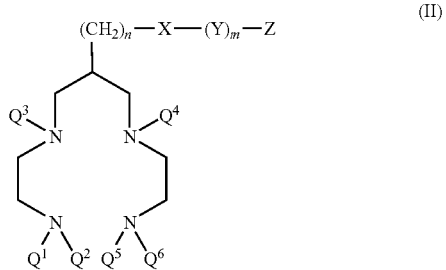

where: X, Y, Z, n and m are as defined above;
$Q^1$ to $Q^6$ are independently Q groups, where Q is H or an amine protecting group.

The chelator conjugates are useful in the preparation of the technetium complexes of Formula I of the first embodiment.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Amine protecting groups are well known to those skilled in the art and are suitably chosen from: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl). In some instances, the nature of the protecting group may be such that both the $Q^1/Q^2$ or $Q^5/Q^6$ groups, ie. there is no NH bond on the associated amine nitrogen atom. The use of further protecting groups are described in 'Protective Groups in Organic Synthesis', Theorodora W. Greene and Peter G. M. Wuts, (John Wiley & Sons, 1991). Preferred amine protecting groups are Boc and Fmoc, most preferably Boc. When Boc is used, $Q^1$ and $Q^6$ are both H, and $Q^2$, $Q^3$, $Q^4$ and $Q^5$ are each tert-butoxycarbonyl.

In Formula II, the amine protecting groups are employed primarily to protect the amine functional groups of the tetraamine chelator during the synthetic chemistry prior to complexation with the technetium. When the biological targeting group (Z) is susceptible to reaction with primary and/or secondary amines, however, these protecting groups may also be useful to prevent undesirable chemical reactions between the chelator amines and Z before complexation with technetium.

Preferred conjugates of Formula II have at least one of the amine nitrogens unprotected (ie. one of $Q^3$ or $Q^4$ is H, or both $Q^1/Q^2$ or $Q^5/Q^6$ are H). One or more free amine groups means that the conjugate is more readily soluble in aqueous media, which is the preferred solvent for the preparation of the technetium complex of Formula I. A free amine group also means that complexation with technetium is more rapid, since complexation is not dependant on prior removal of a protecting group, which would also prevent metal complexation. When the conjugated biological targeting group (Z) is not susceptible to further reaction with amines, it is convenient to use the conjugate of Formula II in the fully deprotected form (ie. each of $Q^1$ to $Q^6$ is H), and this is an especially preferred chelator conjugate of Formula II. The fully deprotected form is preferred for the complexation reaction to give the technetium complex of Formula I.

The technetium complexes of Formula I of the present invention may be prepared by reaction of a solution of the radiometal in the appropriate oxidation state with the chelator conjugate of Formula II at the appropriate pH. The solution may optionally contain a ligand which complexes weakly to the technetium (such as gluconate or citrate) i.e. the technetium complex is prepared by ligand exchange or transchelation. Such conditions are often useful to suppress undesirable side reactions such as hydrolysis of the technetium ion, but are less important with the chelators of the present invention, since they complex rapidly with technetium. When the radioisotope is $^{99m}$Tc, the usual starting material is sodium pertechnetate from a $^{99}$Mo generator. Technetium is present in $^{99m}$Tc-pertechnetate in the Tc(VII) oxidation state, which is relatively unreactive. The preparation of technetium complexes of lower oxidation state Tc(I) to Tc(V) therefore usually requires the addition of a suitable pharmaceutically acceptable reducing agent such as sodium dithionite, sodium bisulphite, ascorbic acid, formamidine sulphinic acid, stannous ion, Fe(II) or Cu(I), to facilitate complexation. The pharmaceutically acceptable reducing agent is preferably a stannous salt, most preferably stannous chloride, stannous fluoride or stannous tartrate.

The chelator conjugates of Formula II may be prepared by conjugation of the biological targeting molecule (Z) with a bifunctional chelator of Formula III, as is described in the fifth embodiment below.

In a third embodiment, the present invention provides a radiopharmaceutical which comprises the technetium complex of the first embodiment, wherein A is a pharmaceutically acceptable counterion, together with a biocompatible carrier in a form suitable for human administration.

By the phrase "in a form suitable for human administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (eg. blood). Such compositions also contain only biologically compatible excipients, and are preferably isotonic.

The "biocompatible carrier" is a fluid, especially a liquid, in which the radiopharmaceutical is suspended or preferably dissolved, such that the composition is physiologically tolerable, ie. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like).

By the term "pharmaceutically acceptable counterion" is meant an anion (i.e. a negative ion) which does not produce toxic or adverse effects when administered to the mammalian body in vivo, and is compatible chemically and/or toxicologically with the other ingredients of the pharmaceutical composition. Chemical compatibility for the technetium radiopharmaceuticals of the present invention means that the anion does not compete effectively with the tetra-amine chelator for the technetium. Suitable such anions include, but are not limited to: halides (e.g., chloride, iodide, and bromide); $C_{1-2}$ alkylsulfonates (e.g., mesylate or ethylsulfonate); arylsulfonates (e.g. phenylsulfonate or tosylate); $C_{1-2}$ alkylphosphonates; di($C_{1-2}$)alkylphosphates (e.g., dimethylphosphate, diethylphosphate, or diglycerol phosphate); arylphosphonates; arylphosphates; alkylarylphosphonates; alkylarylphosphates; $C_{1-2}$ alkylcarboxylates (e.g. acetates, propionates, glutamates or glycerates); arylcarboxylates (eg. benzoates), and the like. Preferred pharmaceutically acceptable counterions are: chloride, fluoride, acetate, tartrate, hydroxide and phosphate.

Such radiopharmaceuticals are suitably supplied in either a container which is provided with a seal which is suitable for single or multiple puncturing with a hypodermic needle (e.g. a crimped-on septum seal closure) whilst maintaining sterile integrity. Such containers may contain single or multiple patient doses. Preferred multiple dose containers comprise a single bulk vial (e.g. of 10 to 30 cm³ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, and are therefore preferably a disposable or other syringe suitable for clinical use. The pre-filled syringe may optionally be provided with a syringe shield to protect the operator from radioactive dose. Suitable such radiopharmaceutical syringe shields are known in the art and preferably comprise either lead or tungsten.

Preferred radiopharmaceuticals of the present invention comprise the technetium radioisotopes $^{99m}$Tc or $^{94m}$Tc, most preferably $^{99m}$Tc. When the technetium isotope is $^{99m}$Tc, a radioactivity content suitable for a diagnostic imaging radiopharmaceutical is in the range 180 to 1500 MBq of $^{99m}$Tc, depending on the site to be imaged in vivo, the uptake and the target to background ratio.

The technetium radiopharmaceuticals of the present invention may be prepared by various methods:
   (i) aseptic manufacture techniques in which the technetium complex formation described above for the second embodiment is carried out in a clean room environment;
   (ii) terminal sterilisation, in which the technetium complex formation is carried out without using aseptic manufacture and then sterilised at the last step (eg. by gamma irradiation or autoclaving);
   (iii) kit methodology in which a sterile, lyophilized non-radioactive kit formulation comprising the chelator conjugate of Formula II and a pharmaceutically acceptable reductant is reacted with plus other optional excipients is reacted with an aliquot of sterile $^{99m}$Tc-pertechnetate from a $^{99m}$Tc generator.

Method (iii) is preferred, and kits for use in this method are described in the fourth embodiment (below).

In a fourth embodiment, the present invention provides a non-radioactive kit for the preparation of the radiopharmaceutical composition described above, which comprises the conjugate of Formula (II), together with a biocompatible reductant. Such kits are designed to give sterile radiopharmaceutical products suitable for human administration, e.g. via direct injection into the bloodstream. The ligand conjugates, and preferred aspects thereof, are described in the second embodiment above.

For $^{99m}$Tc, the kit is preferably lyophilised and is designed to be reconstituted with sterile $^{99m}$Tc-pertechnetate (TcO$_4^-$) from a $^{99m}$Tc radioisotope generator to give a solution suitable for human administration without further manipulation. Suitable kits comprise a container (eg. a septum-sealed vial) containing the chelator conjugate in either free base or acid salt form, together with a biocompatible reductant such as sodium dithionite, sodium bisulphite, ascorbic acid, formamidine sulphinic acid, stannous ion, Fe(II) or Cu(I). The biocompatible reductant is preferably a stannous salt such as stannous chloride or stannous tartrate. Alternatively, the kit may optionally contain a non-radioactive metal complex which, upon addition of the technetium, undergoes transmetallation (i.e. metal exchange) giving the desired product.

The non-radioactive kits may optionally further comprise additional components such as a transchelator, radioprotectant, antimicrobial preservative, pH-adjusting agent or filler. The "transchelator" is a compound which reacts rapidly to form a weak complex with technetium, then is displaced by the chelator. This minimises the risk of formation of reduced hydrolysed technetium (RHT) due to rapid reduction of pertechnetate competing with technetium complexation. Suitable such transchelators are salts of a weak organic acid, ie. an organic acid having a pKa in the range 3 to 7, with a biocompatible cation. By the term "biocompatible cation" is meant a positively charged counterion which forms a salt with an ionised, negatively charged anionic group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium. Suitable such weak organic acids are acetic acid, citric acid, tartaric acid, gluconic acid, glucoheptonic acid, benzoic acid, phenols or phosphonic acids. Hence, suitable salts are acetates, citrates, tartrates, gluconates, glucoheptonates, benzoates, phenolates or phosphonates. Preferred such salts are tartrates, gluconates, glucoheptonates, benzoates, or phosphonates, most preferably phosphonates, most especially diphosphonates. A preferred such transchelator is a salt of MDP, ie. methylenediphosphonic acid, with a biocompatible cation.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (ie. 4-aminobenzoic acid), gentisic acid (ie. 2,5-dihydroxybenzoic acid) and salts thereof with a biocompatible cation as described above.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the radiopharmaceutical composition post-reconstitution, ie. in the radioactive diagnostic product itself. The antimicrobial preservative may, however, also optionally be used to inhibit the growth of potentially harmful micro-organisms in one or more components of the non-radioactive kit of the present invention prior to reconstitution. Suitable antimicrobial preservative(s) include: the parabens, ie. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human or mammalian administration. Suitable such pH-adjusting agents include pharmaceutically acceptable buffers, such as tricine, phosphate or TRIS [ie. tris(hydroxymethyl)aminomethane], and pharmaceutically acceptable bases such as sodium carbonate, sodium bicarbonate or mixtures thereof. When the conjugate is employed in acid salt form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable such fillers include inorganic salts such as sodium chloride, and water soluble sugars or sugar alcohols such as sucrose, maltose, mannitol or trehalose.

In a fifth embodiment, the present invention provides a compound of Formula III:

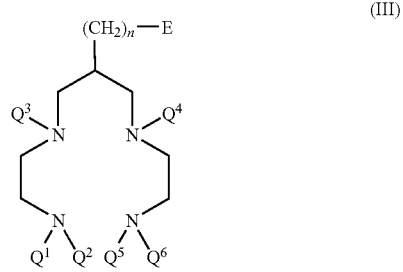

(III)

where: $Q^1$ to $Q^6$ and n are as defined for Formulae I and II above;

E is a functional group suitable for conjugation to the biological targeting moiety (Z) of the first embodiment;

with the provisos that:

(i) when n=3, then at least one of $Q^1$ to $Q^6$ is an amine protecting group;

(ii) when n=3 or 5, E is not OH.

The compound of Formula III is a "bifunctional chelator", ie. a chelating agent with one or more functional groups (E) attached. The functional group E is suitable for conjugation to the biological targeting moiety (Z). Suitable such functional groups (E) include: amine, thiocyanate, maleimide and active esters. E preferably does not comprise an inactivated hydroxyl (—OH) group. By the term "active ester" is meant an ester derivative of the carboxylic acid which is designed to be a better leaving group, and hence permit more facile reaction with nucleophiles present on the biological targeting moiety such as amines. Examples of suitable active esters are: N-hydroxysuccinimide (NHS), pentafluorophenol, pentafluorothiophenol, para-nitrophenol, hydroxybenzotriazole and PyBOP (ie. benzotriazol-1-yl-oxytripyrrolidinophosphonium hexafluorophosphate). Preferred active esters are N-hydroxysuccinimide or pentafluorophenol esters.

E is preferably primary amine (—NH$_2$), —CO$_2$M, —NCS, —NCO, maleimide or acrylamide, where M is H, a cation, a protecting group or an active ester. E is most preferably —NH$_2$, —CO$_2$M or maleimide, ideally —NH$_2$ or —CO$_2$M.

The compound of Formula III is reacted with suitable counterpart functional groups on the biological targeting molecule (Z) to form the desired conjugate of Formula II.

Such suitable functional groups on the biological targeting molecule include:

carboxyls (for amide bond formation with an amine-functionalised bifunctional chelator);

amines (for amide bond formation with an carboxyl- or active ester-functionalised bifunctional chelator);

halogens, mesylates and tosylates (for N-alkylation of an amine-functionalised bifunctional chelator) and thiols (for reaction with a maleimide-functionalised bifunctional chelator).

When E is a group (eg. an active ester) which is designed to react with an amine group of the biological targeting molecule (Z), clearly there is a potential for undesirable side reactions with the amines of the chelator. For such E groups, $Q^1$ to $Q^6$ in Formula III are preferably chosen to be nitrogen protecting groups such that each of the four amine nitrogen atoms of the tetra-amine chelator are protected. When E is an amine group, it is clearly important that reaction with the biological targeting molecule (Z) occurs only at the E amine, and not at the amine nitrogen atoms of the tetra-amine chelator. In that situation also therefore, $Q^1$ to $Q^6$ in Formula III are preferably nitrogen protecting groups. Nitrogen protecting groups, and preferred examples thereof, are described in the second embodiment (above).

The compounds of Formula III may be prepared as described in Schemes 1 and 2. Scheme 1 provides a flexible synthetic route to carboxy-functionalised, N-protected tetra-amine chelators, which can be adapted to a variety of values of n in Formula III. The synthesis of the Boc-protected tetra-amine analogue with a —(CH$_2$)$_5$OH bridgehead substituent has been described by Turpin et al [J. Lab. Comp. Radiopharm., 45, 379-393 (2002)]. Scheme 2 provides a flexible synthetic route to amine-functionalised, N-protected tetra-amine chelators, which can be adapted to a variety of values of n. The conjugation of biological targeting peptides can be carried in an analogous manner to those described by Nock et al [Eur. J. Nucl. Med., 30(2), 247-258 (2003)], and Maina et al [Eur. J. Nucl. Med., 30(9), 1211-1219 (2003)].

13
Scheme 1: Synthesis of Compound 1.
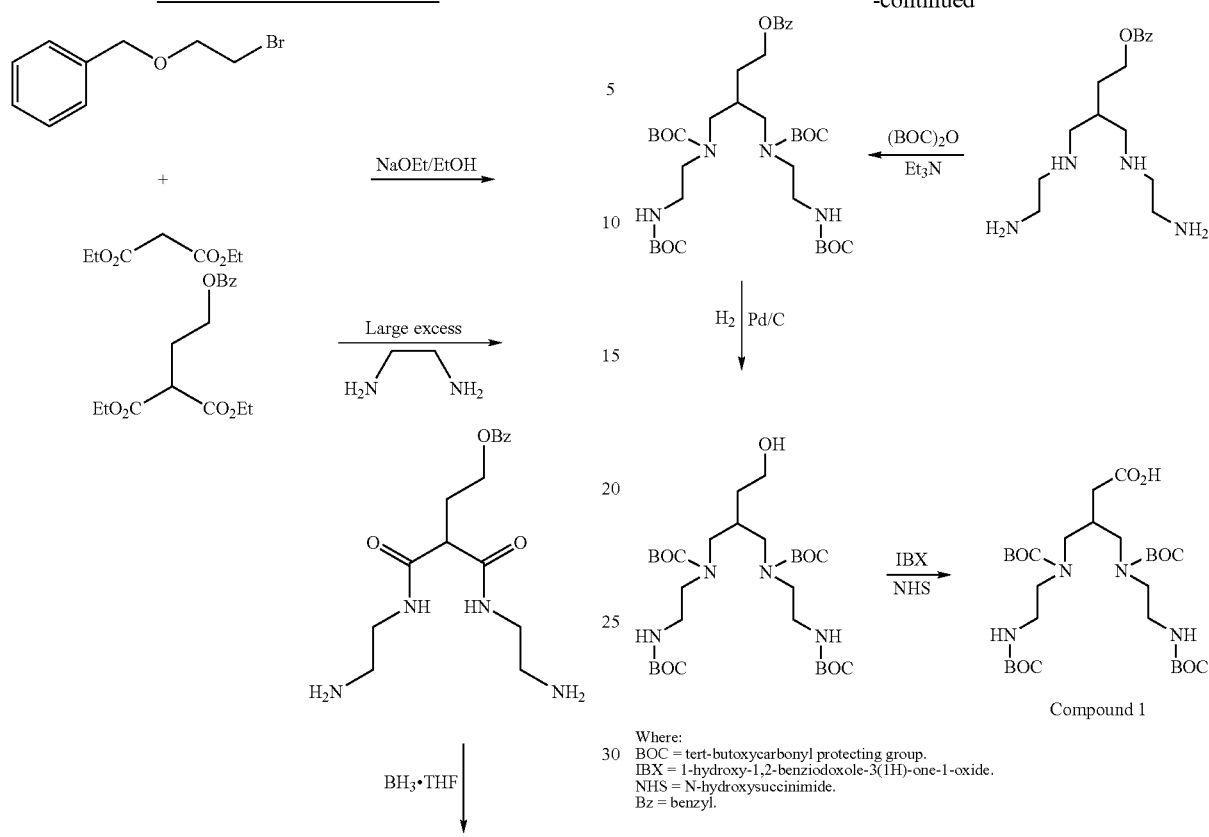
Where:
BOC = tert-butoxycarbonyl protecting group.
IBX = 1-hydroxy-1,2-benziodoxole-3(1H)-one-1-oxide.
NHS = N-hydroxysuccinimide.
Bz = benzyl.
Scheme 2: Synthesis of Compound 2.
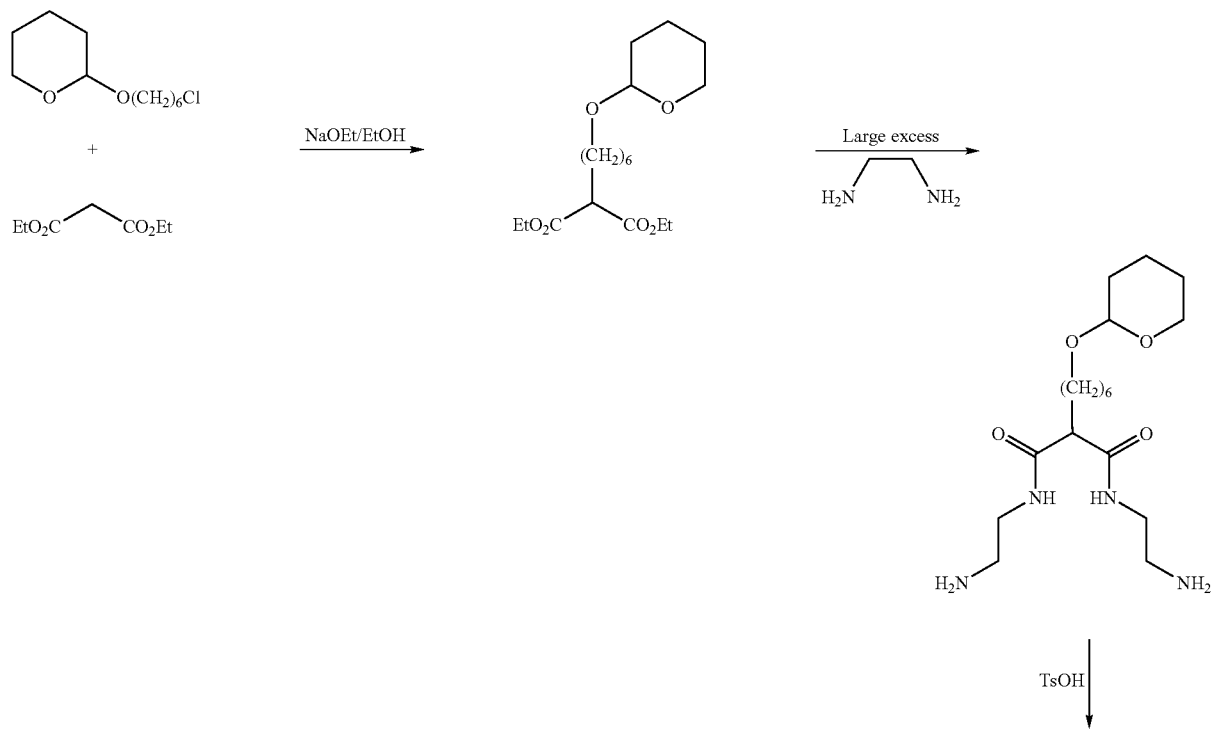

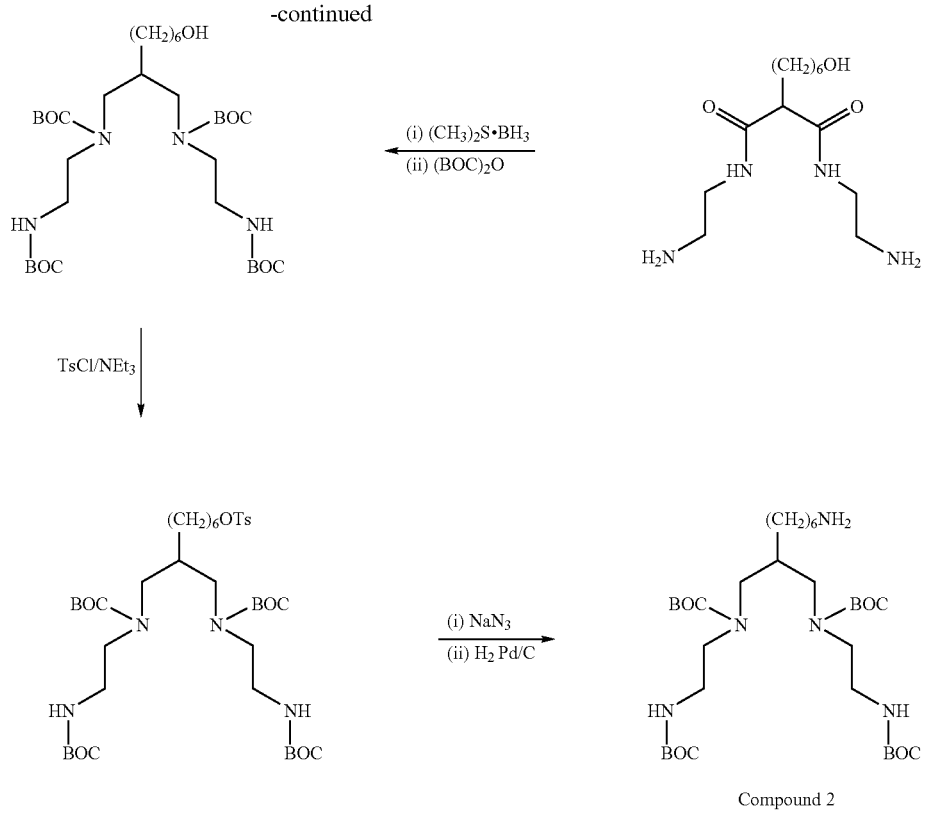

where:
Ts = p-toluenesulfonyl

The invention is illustrated by the following non-limiting Examples. Example 1 provides the synthesis of Compound 1, a carboxy-functionalised N-protected tetraamine chelator of the present invention. Example 2 provides the synthesis of Compound 2, an amine-functionalised N-protected tetraamine chelator of the present invention. Example 3 provides the synthesis of Compound 3, a compound showing conjugation of Compound 1 with an amine (benzylamine). Example 4 describes the synthesis of Compound 6, illustrating the conjugation of Compound 2 with an active ester of a carboxylic acid. Example 5 describes the synthesis of Compound 4, a conjugate of a chelator of the invention with a losaratan derivative. Example 6 provides the synthesis of a losartan chelator conjugate including a PEG linker group. Example 7 describes the synthesis of Compound 8, an angiotensin peptide conjugate of a chelator of the invention. Example 8 describes the $^{99m}$Tc-radiolabelling of several chelators of the invention. Example 9 shows the measurement of lipophilicity (logP) values for various $^{99m}$Tc complexes of the invention, and shows that the complexes are relatively hydrophilic. Example 10 shows the biodistribution results for several $^{99m}$Tc complexes of the invention, showing modest liver background, and high urinary clearance. Example 11 provides a higher-yielding synthesis of Compound 1. Example 12 provides the synthesis of a protected tetraamine chelator of the present invention having conjugated thereto an activated ester (Compound 9).

EXAMPLE 1

Synthesis of Compound 1

Step (a): Diethyl [2-(benzyloxy)ethyl]malonate

The compound was prepared by a modification of the method of Ramalingam et al *Tetrahedron*, 51, 2875-2894 (1995)]. Thus, sodium (1.20 g) was dissolved in absolute ethanol (25 mL) under argon. Diethyl malonate (14.00 g) was added and the mixture was refluxed for 30 min. Benzyl bromoethyl ether (10 g) was added and the mixture was stirred at reflux for 16 hours. The ethanol was removed by rotary evaporation and the residue was partitioned between ether (100 mL) and water (50 mL). The ethereal layer was washed with water (3×50 mL) and dried over sodium sulfate. The ether was removed by rotary evaporation and the residue was distilled in vacuoo. The fraction distilling at 40-55° C. was discarded (unreacted diethyl malonate). The product distilled at 140-150° C. (1 mm), [lit. bp 138-140 C (1 mm)]. The yield was 12.60 g of colourless oil.

$^{1}$H NMR (270 MHz, CDCl$_3$, 25° C., TMS) δ=7.28 (m, 5H C$_6$H$_5$), 4.47 (s, 2H, CH$_2$-Ph), 4.16 (m, 4H, COOCH$_2$), 3.58 (t, 1H, CH), 3.50 (t, 2H, O—CH$_2$—CH$_2$), 2.21 (t, 2H, O—CH$_2$—CH$_2$), 1.20 (t, 6H, COOCH$_2$—CH$_3$). $^{13}$C NMR (67.5 MHz, CDCl$_3$, 25° C., TMS) δ=169.20 (CO), 138.10, 128.60, 127.80 (aromatic), 73.00 (CH$_2$Ph), 67.30 (O—Ch$_2$—

$CH_2$), 61.70 ($COOCH_2$), 49.10 (CH), 28.90 (O—$Ch_2$—$CH_2$), 14.10 ($COOCH_2CH_3$).

Step (b): N,N'-Bis(2-aminoethyl-2-(2-benzyloxy-ethyl)malonamide

Diethyl [2-(benzyloxy)ethyl]malonate (4.00 g) was added to ethylene diamine (30 mL) and the solution was stirred at room temperature for two days. The excess ethylene diamine was removed by rotary evaporation and the residue was dried under high vacuum for 2 days to give a yellow oil (4.28 g) that crystallized on standing. The product still contained traces of ethylenediamine, as detected in the NMR spectra.

$^1$H NMR (270 MHz, $CDCl_3$, 25° C., TMS) δ=7.74 (br t, 2H, CO—NH), 7.32 (m, 5H, $C_6H_5$), 4.46 (s, 2H, $CH_2$—Ph), 3.50 (t, 2H, $OCH_2$—$CH_2$—), 3.33 (t 1H, CH), 3.23 (m, 4H, CO—NH—$CH_2$), 2.74 (t, 4H, $CH_2$—$NH_2$) 2.18 (q, 2H, O—$Ch_2$—$CH_2$—) 1.55 (br s 4H, $NH_2$). $^{13}$C NMR (67.5 MHz, $CDCl_3$, 25° C., TMS) δ=171.10 (CO), 138.20, 128.30, 127.70 (aromatic), 73.00 ($CH_2$—Ph), 67.80 (O—$Ch_2$—$CH_2$), 51.40 (CH), 42.40 (CO—NH—$CH_2$), 41.20 ($CH_2$—$NH_2$), 31.90 (O—$CH_2$—$CH_2$—).

Step (c): N,N'-Bis(2-amino-ethyl)-2-(2-benzyloxy-ethyl)-1,3-diaminopropane

N,N'-Bis-(2-aminoethyl)-2-(2-benzyloxy-ethyl)malonamide (3.80 g) was dissolved in THF (20 mL) and the flask was immersed in an ice bath. The flask was flushed with argon and THF borane complex (80 mL, 1 M in THF) was added through a syringe. The reaction mixture was allowed to warm up to room temp. and then stirred at 40° C. for 2 days and refluxed for 1 h. Methanol (50 mL) was added dropwise and the solution was stirred at 40 overnight. The solvents were removed by rotary evaporator and the residue was dissolved in methanol (20 mL). Sodium hydroxide (10 g in 15 mL of water) was added and the methanol was boiled away. A colourless oil separated that was extracted into $CH_2Cl_2$ (3×50 mL). The solution was dried over $Na_2SO_4$. Removal of the solvent gave 3.40 g of colourless oil.

$^1$H NMR (270 MHz, $CDCl_3$, 25° C., TMS) δ=7.34 (m, 5H, $C_6H_5$), 4.49 (s, 2H, $CH_2$—Ph), 3.55 (t, 2H, $OCH_2$—$CH_2$—), 2.76 (t, 4H, N—$CH_2$), 2.63 (m, 8H, N—$CH_2$), 1.84 (m, 1H, CH), 1.58 (m, 2H, CH—$CH_2$—$CH_2$—O), 1.41 (br s, 6H, NH). $^{13}$C NMR (67.5 MHz, $CDCl_3$, 25° C., TMS) δ=138.60, 128.30, 127.60 (aromatic), 72.80 ($CH_2$—Ph), 68.70 (O—$Ch_2$—$CH_2$), 53.50 (N—$CH_2$), 52.80 (N—$CH_2$), 41.60 (N—$CH_2$) 36.40 (CH), 31.30 (CH—$CH_2$—$CH_2$—O). MS-EI: 295 [M+H]$^+$, (calcd.: 295.2).

Step (d): N,N'-Bis(2-tert-butoxycarbonylamino-ethyl-2-(2-benzyloxyethyl)-1,3-di(tert-butoxycarbonylamino)propane N,N'-Bis(2-aminoethyl)-2-(2-benzyloxy-ethyl)-1,3-diaminopropane (3.30 g) was dissolved in $CH_2Cl_2$ (100 mL) and triethylamine (5.40 g) and tert-butyl dicarbonate (10.30 g) were added. The reaction mixture was stirred at room temp. for 2 days. The mixture was washed with water (100 mL), citric acid solution (100 mL, 10% in water) and with water (2×100 mL). The organic layer was dried over $Na_2SO_4$, and the solvent was removed by rotary evaporation giving a yellow oil which was dried to a constant mass under high vacuum. The crude product (7.70 g) was purified on a silica gel column (250 g, 230-400 mesh, $CH_2Cl_2$, $CH_2Cl_2$-$Et_2O$ 1:1) to give 6.10 g (78.3%) of a clear oil.

$^1$H NMR (270 MHz, $CDCl_3$, 25° C., TMS) δ=7.32 (m, 5H, $C_6H_5$), 5.12 (br d, 2H, NH), 4.47 (s, 2H, $CH_2$—Ph), 3.49 (t, 2H, $OCH_2$—$CH_2$—), 3.24 (br, 12H, N—$CH_2$), 2.14 (br, 1H, CH), 1.59 (m, 2H, CH—$CH_2$—$CH_2$—O) 1.45 (s, 18H, t-Bu), 1.42 (s, 18H, t-Bu). $^{13}$C NMR (67.5 MHz, $CDCl_3$, 25° C., TMS) δ=155.90 (NH—CO), 138.20, 128.30 127.60, 127.50 (aromatic), 79.90, 78.90 ($CMe_3$), 72.80 ($CH_2$-Ph), 68.00 (O—$Ch_2$—$CH_2$), 50.00 (br, N—$CH_2$), 46.90 (br, N—$CH_2$), 39.20 (N—$CH_2$), 34.40 (br, CH), 29.80 (CH—$CH_2$—$CH_2$—O), 28.30 (t-Bu). MS-EI: 695 [M+H]$^+$, (calcd.: 695.5)

Step (e): N,N'-Bis(2-tert-butoxycarbonylamino-ethyl)-2-(2-hydroxyethyl)-1,3-di(tert-butoxycarbonylamino)propane N,N'-Bis(2-tert-butoxycarbonylamino-ethyl)-2-(2-benzyloxy-ethyl)-1,3-di(tert-butoxycarbonylamino)propane (3.16 g) was dissolved in absolute ethanol (100 mL) and Pd on activated carbon (1.00 g, dry, 10%) was added. The mixture was hydrogenated in a Parr hydrogenation apparatus at 35 psi for two days. The catalyst was filtered off, washed with ethanol (3×20 mL). The ethanol was removed by rotary evaporation to give a colourless oil that was dried to a constant mass (2.67 g, 97.1%) under high vacuum.

$^1$H NMR (270 MHz, $CDCl_3$, 25° C., TMS) δ=5.25 (br d, 2H, NH), 3.69 (t, 2H, $OCH_2$—$CH_2$—), 3.28 (br, 12H, N—$CH_2$), 2.71 (br, OH), 2.23 (br, 1H, CH), 1.56 (shoulder, m, 2H, CH—$CH_2$—$CH_2$—O) 1.48 (s, 18H, t-Bu), 1.44 (s, 18H, t-Bu). $^{13}$C NMR (67.5 MHz, $CDCl_3$, 25° C., TMS) δ=156.10 (NHCO), 80.00, 79.20 ($CMe_3$), 59.60 (O—$Ch_2$—$CH_2$), 49.90 (br, N—$CH_2$), 47.00 (br, N—$CH_2$), 39.34 (N—$CH_2$), 33.80 (CH), 32.30 (CH—$CH_2$—$CH_2$—O), 28.30 (t-Bu). MS-EI: 605 [M+H]$^+$, (calcd.: 605.4).

Step (f): N,N'-Bis(2-tert-butoxycarbonylamino-ethyl-2-(2-carboxymethyl-1,3-di(tert-butoxycarbonylamino)propane (Compound 1)

The method of Mazitschek et al [*Ang. Chem. Int. Ed.*, 41, 4059-4061 (2002)] was used. Thus, N,N'-Bis(2-tert-butoxycarbonylamino-ethyl)-2-(2-hydroxyethyl)-1,3-di(tert-butoxycarbonylamino)propane (2.60 g) was dissolved in DMSO (15 mL) and 1-hydroxy-1,2-benziodoxole-3(1H)-one-1-oxide (IBX, 3.50 g) was added. The mixture was stirred at room temp. for 1 hour then N-hydroxysuccinimide (2.50 g) was added. The reaction mixture was stirred at room temp. for 2 days. Sodium hydroxide solution (2M, 40 mL) was added and the mixture was stirred at room temp. for 4 hours. The solution was immersed in an ice bath and was acidified with 2M hydrochloric acid to pH 2. The aqueous layer was extracted with ether (4×100 ml) and the combined ether extracts were washed with water (3×50 mL). The ethereal layer was dried over $Na_2SO_4$ and the solvent was removed by rotary evaporation to give a yellow solid residue that contained the product and 2-iodosobenzoic acid. Most of the iodosobenzoic acid (2.1 g) was removed by crystallization from chloroform-hexanes (1:3) (80 mL). Evaporation of the chloroform-hexanes mother liquor gave a yellow oil (3 g) that was loaded on a silica column (300 g, $CH_2Cl_2$—$Et_2O$, 1:1). The remaining iodosobenzoic acid was eluted with ether. The product was eluted with ether-methanol (9:1). The fractions containing the product were combined and removal of the solvent gave 1.5 g of pale yellow oil. This was rechromatographed on a silica column (50 g, $Et_2O$). The product was eluted with ether-acetic acid (95:5). The fractions containing the product were combined and the solvent was removed by rotary evaporation to give an oil that was dried under high vacuum. The yield was 1.10 g (41.3%).

$^1$H NMR (270 MHz, CDCl$_3$, 25° C., TMS) δ=7.61 (br s, 1H, COOH), 5.19 (br d, 2H, NH), 3.22 (br, 12H, N—CH$_2$), 2.47 (br m, 1H, CH), 2.26 (br, 2H, CH—CH$_2$—COOH), 1.41 (s, 18H, t-Bu), 1.37 (s, 18H, t-Bu). $^{13}$C NMR (67.5 MHz, CDCl$_3$, 25° C., TMS) δ=175.90 (COOH), 156.10 (NHCO), 80.40, 79.10 (CMe$_3$), 49.50 (N—CH$_2$), 46.80 (N—CH$_2$), 39.00 (N—CH$_2$), 34.70 (CH—CH$_2$—COOH), 34.20 (CH—CH$_2$—COOH), 28.30 , 28.20 (t-Bu). MS-EI: 619 [M+H]$^+$, (calcd.: 619.4).

EXAMPLE 2

Synthesis of (8-Amino-2-{[tert-butoxycarbonyl-(2-tert-carbonylamino-ethyl)-amino]-methyl}-octyl)-(2-tert-butyloxycarbonylamino-ethyl)-carbamic acid tert-butyl ester (Compound 2)

Step (a): 2-(6-Chloro-hexyloxy)tetrahydropyran

6-Chlorohexanol (6.85 g, 10 mmol) and p-toluenesulphonic acid (500 mg), were dissolved in dry ether (75 ml) and cooled to 0-5° C. in an ice bath. Dihydropyran (4.3 g, 10 mmol) in dry ether (25 ml) was added dropwise with constant stirring over a 30 minute period. After complete addition, the cooling bath was removed and stirring continued for 16 hours. The solution was extracted with water (50 ml×2), dried (MgSO$_4$), filtered and the solvent evaporated under reduced pressure to leave a pale yellow oil. This oil was shown by $^{13}$C NMR spectroscopy to be sufficiently pure to be used without purification in the subsequent reactions. Yield 10.1 g (91%).

$^{13}$C NMR (CDCl$_3$): δ 19.7 (CH$_2$), 25.5 (CH$_2$), 25.6 (CH$_2$), 26.7 (CH$_2$), 29.6 (CH$_2$), 30.8 (CH$_2$), 32.6 (CH$_2$), 45.0 (CH$_2$Cl), 62.3 (OCH$_2$), 67.4 (OCH$_2$), 98.8 (OCHO).

$^1$H NMR (CDCl$_3$): δ 1.30-1.71 (14H, m, CH$_2$×7), 3.24-3.32 (1H 3.41-3.48 (3H, m CH and CH$_2$), 3.60-3.67 (1H, m, CH), 3.72-3.82 (1H, bm, CH), 4.44-4.49 (1H, bm, OCHO).

Step (b): 2-[6-(Tetrahydro-pyran-2-yloxy)-hexyl]-malonic acid diethyl ester

Sodium (1.13 g, 49 mmol) in small quantities was dissolved in dry ethanol (100 ml) with constant stirring under a blanket of dry nitrogen. Diethyl malonate (8.0 g, 50 mmol) was added in one portion and the solution heated at 60° C. for 1 hour. 2-(6-Chloro-hexyloxy)-tetrahydropyran (9.3 g, 42.2 mmol) was added in one portion and the temperature raised to 75-80° C. and maintained at this level for 24 hours. After cooling, the inorganic solid was removed by filtration and solvent evaporated from the filtrate. The residue was dissolved in CH$_2$Cl$_2$ (50 ml), extracted with water (30 ml×2), dried (MgSO$_4$) filtered and volatiles removed to leave a pale yellow oil. This oil was subject to chromatography on silica gel using pet ether 40:60/ether (200:40) as the eluent. The required product eluted with an r$_f$=0.15 and was isolated as a colourless oil. Yield 8.7 g, (60%).

$^{13}$C NMR (CDCl$_3$): δ 14.0 (CH$_3$×2), 19.6 (CH$_2$), 25.5 (CH$_2$), 27.2 (CH$_2$), 28.6 (CH$_2$), 29.0 (CH$_2$), 29.6 ((CH$_2$), 30.0 (CH$_2$), 30.8 (CH$_2$), 52.0 (CH), 61.2 (OCH$_2$×2), 62.2 (OCH$_2$), 67.4 (OCH$_2$), 98.8 (OCHO), 169.4 (C═O×2).

$^1$H NMR (CDCl$_3$): δ 1.10-1.25 (14H, m, CH$_3$×2, CH$_2$×4), 1.36-1.50 (6H, bm, CH$_2$×3), 1.70-1.81 (2H, bm, CH$_2$), 3.17-3.28 (2H, m, CH$_2$), 3,56-3.66 (1H, m, CH), 3.70-3.80 (1H, m, OCH), 4.04-4.16 (4H, m, OCH$_2$×2), 4.03-4.08 (1H, m, OCHO).

Step (c): N,N'-Bis-(2-amino-ethyl)-2-[6-(tetrahydro-pyran-2-yloxy)-hexyl]-malonamide 2-[6-(Tetrahyhdro-pyran-2-yloxy)-hexyl]-malonic acid diethyl ester (5.1 g, 14.8 mmol) was dissolved in 1,2-diaminoethane (10 g, 167 mmol) and stirred at room temperature for 16 hours. Volatiles were removed in vacuo (40-50° C. at 0.01 mm Hg) to leave a pale green viscous residue which was subjected to column chromatography eluting with CH$_2$Cl$_2$/MeOH/NH$_4$OH (50:50:5). The title compound eluted with an r$_f$ 0.2 and was collected as a pale green viscous oil which solidifies on standing. (Yield 3.9 g, 71%).

$^{13}$C NMR (CDCl$_3$): δ 19.8 (CH$_2$), 25.5 (CH$_2$), 26.0 (CH$_2$), 27.5 (CH$_2$), 29.2 (CH$_2$), 29.7 (CH$_2$), 30.8 (CH$_2$), 31.9 (CH$_2$), 41.0 (NCH$_2$×2), 41.9 (NCH$_2$×2), 54.6 (CH), 62.5 (OCH$_2$), 67.5 (OCH$_2$), 98.9 (OCHO), 171.6 (C═O×2).

$^1$H NMR (CDCl$_3$): δ 1.15-1.28 (6H, bs, CH$_2$×3), 1.39-1.44 (6H, bm, CH$_2$×3), 1.69-1.74 (4H, bm, CH$_2$×2), 2.64 (4H, bs, NH$_2$×2), 2.73 4H, t, J=6 Hz, CH$_2$×2), 3.08-3.29 (6H, m, CH$_2$×3), 3.35-3.41 (1H, m CH), 3.55-3.63 (1H, m, CH), 3.70-3.78 (1H, m, CH), 4.43 (1H, bt, J=4 Hz, OCHO), 7.78 (2H, bt, J=5 Hz, OCNH×2)

IR (thin film) cm$^{-1}$: 3417, 3082, 2936, 2862, 1663, 1558, 1439,1354, 1323, 1261, 1200, 1189, 1076, 1026, 956, 907, 867, 810.

Step (d): N,N'-Bis(2-aminoethyl)-2-(6-hydroxy-hexyl)-malonamide

N,N'-Bis(2-aminoethyl)-2-[6-(tetrahydro-pyran-2-yloxy)-hexyl]-malonamide (3.9 g, 10.6 mmol), p-toluenesulphonic acid monohydrate (8.5 g, 3 mmol) and ethanol (50 ml) were heated under reflux at 70-75° C. for 16 hours. After cooling, concentrated ammonium hydroxide (0.880) was added dropwise until a permanent pH of 9 was achieved. The precipitated white solid was removed by filtration through Celite and the filter cake washed with ethanol (30 ml). The ethanol was removed under reduced pressure (15 mm Hg, 40° C.) to leave a semi-solid wax. This residue was subjected to chromatography on silica-gel eluting with CH$_2$Cl$_2$/MeOH/NH$_4$OH (100:50:10) and the title compound found to have an r$_f$=0.2. This product was collected and co-evaporated with ethanol (100 ml×3) to remove any residual water. A pale green viscous residue was obtained which solidifies on standing. (Yield 2.1 g, 69%).

$^{13}$C NMR (CD$_3$OD): δ 25.4 (CH$_2$), 27.3 (CH$_2$), 28.9 (CH$_2$), 30.4 (CH$_2$), 32.2 (CH$_2$), 40.6 (NCH$_2$×2), 41.7 (NCH$_2$×2), 54.1 (CH), 61.6 (CH$_2$OH), 171.7 (C═O×2).

$^1$H NMR (CD$_3$OD): δ 1.28-1.38 (6H, bs, CH$_2$ ×3), 1.46-1.55 (2H, bm, CH$_2$), 1.79-1.87 (2H, bm, CH$_2$), 2.73 (4H, t, J=6 Hz, H$_2$NCH$_2$×2), 3.13 (1H t, J=7 Hz, CH), 3.27 (4H, dt, J=6 and 2 Hz, HNCH$_2$×2), 3.53 (2H t, J=7 Hz OCH$_2$).

IR (thin film) cm$^{-1}$: 3364, 2932, 2862, 2527, 1663, 1558, 1462, 1327, 1223, 1192, 1034.

Mass spec (Fabs) m/e: Calculated for C$_{13}$H$_{29}$N$_4$O$_3$ (M+H) 289 Found 289.

Step (e): (2-tert-Butoxycarbonylamino-ethyl-2-{[tert-butoxycarbonyl-(2-tert-butoxycarbonylamino-ethyl-amino]-methyl}-8-hydroxy-octyl)-carbonic acid tert-butyl ester Under a blanket of dry nitrogen, neat borane-dimethylsulphide adduct (15 ml, 150 mmol) was added dropwise via a syringe to a stirred mixture of N,N'-bis-(2-aminoethyl)-2-(6-hydroxyhexyl)malonamide (2.1 g, 7.3 mmol) in dioxane (50 ml). After complete addition, the mixture was heated gently under reflux at 110° C. for 5 days. During this period some white solid remained. After cooling the volatiles were removed under reduced pressure to leave a white solid to which methanol (50 ml) was added dropwise giving a colourless solution. This solution was heated under reflux for 3 hours, cooled, conc. HCl (5 ml) added and heating continued under reflux at 70-75° C. for 48 hours. The solvent was removed to leave a viscous green residue which was co-evaporated with methanol (100 ml×3) to leave a pale green solid. This solid was redissolved in dry methanol and anhydrous potassium carbonate (4.0 g, 30 mmol) added followed by di-tert-butyl dicarbonate (7.0 g, 32 mmol). The mixture was stirred at room temperature for 48 hours. The inorganic solid was removed by filtration through Celite and solvent evaporated from the filtrate to leave a viscous residue. This residue was mixed with water (50 ml) and extracted with $CH_2Cl_2$ (50 ml×3). The organic fractions were combined, dried ($MgSO_4$), filtered and the solvent evaporated to leave a pale yellow residue.

Note: At this point it is convenient to monitor the reaction by $^{13}C$ NMR. The residue was subjected to chromatography on silica gel using $CH_2Cl_2$/MeOH (95:5) as eluent. The title compound eluted with an $r_f$=0.41 and was isolated as a colourless viscous oil (Yield 2.5 g, 52%).

$^{13}C$ NMR ($CDCl_3$): δ 25.6 ($CH_2$), 26.4 ($CH_2$), 28.4 ($CH_3$× 12), 29.8 ($CH_2$×2), 32.6 ($CH_2$), 36.5 (very broad, CH), 39.2 ($NCH_2$×2, adjacent CH), 46.9 (broad singlet, $HNCH_2$×2), 50.0 (broad singlet, $NCH_2$×2), 62.4 ($HOCH_2$), 79.0 (OC×2), 79.9 (OC×2), 156.4 (broad singlet C=O×4)

$^1H$ NMR ($CDCl_3$): δ 1.05-1.18 (8H, bs, $CH_2$×4), 1.27 (18h, S, $CH_3$×6, t-butyl), 1.31 (18H, s, $CH_3$×6, t-butyl), 1.41 (2H, m, $CH_2$), 1.81 (1H bs, CH), 2.63 (1H, bs, OH), 2.98 (4H, bs, $NCH_2$×2), 3.11 (8H, bs, $NCH_2$×4), 3.44 (2H, t, J=8 Hz, $CH_2O$), 5.2 (2H, bs, NH×2)

IR (thin film) cm$^{-1}$: 3350, 2976, 2931, 2859, 1674, 1516, 1455, 1418, 1393, 1260, 1250, 1165, 1069, 965, 871, 775.

Mass Spec (Fabs) m/e: Calculated for $C_{33}H_{65}N_4O_9$ (M+H) 661 Found 661.

Step (f): Toluene-4-sulfonic acid 8-[tert-butoxycarbonyl-(2-tert-butoxycarbonylamino-ethyl-amino]-7-{[tert-butoxycarbonyl-(2-tert-butoxycarbonylamino-ethyl)-amino]-methyl}-octyl Ester (2-tert-Butoxycarbonylamino-ethyl-2-{[tert-butoxycarbonyl-(2-tert-butoxycarbonylaminoethyl)amino]-methyl}-8-hydroxyoctyl)-carbonic acid tert-butyl ester (2.52 g, 3.82 mmol),p-toluenesulfonyl chloride (1.0 g, 5.2 mmol), triethylamine (1.3 g, 12.8 mmol) and $CH_2Cl_2$ (30 ml) were stirred at room temperature with the slow evaporation of solvent. The reaction was monitored by carbon NMR and after 3 days little starting material remained. The reaction volume was made up to 30 ml with $CH_2Cl_2$, extracted with water (50 ml×3), dried ($MgSO_4$), filtered and the solvent evaporated to leave a brown residue. This residue was subjected to chromatography on silica gel using $CH_2Cl_2$/MeOH (100:5) as eluent. The first compound to elute was unreacted tosyl chloride with an $r_f$=0.95. The title compound eluted with an $r_f$=0.2 and was isolated as a pale yellow viscous oil. Yield (1.20 g, 39%).

$^{13}C$ NMR ($CDCl_3$): δ 21.7 ($CH_3$ tosyl), 25.3 ($CH_2$), 26.3 ($CH_2$), 28.5 ($CH_3$×12), 28.8 ($CH_2$), 29.5 ($CH_2$), 29.9 ($CH_2$), 36.5 (CH very broad), 39.4 ($NCH_2$×2), 47.0 (broad $NCH_2$×2), 50.5 (broad, $NCH_2$×2), 70.6 ($TsOCH_2$), 79.1 (OC×2), 80.0 (OC×2), 127.9 (CH×2), 129.9 (CH×2), 133.2 (C), 144.7 (C-S Ts), 156.1 (broad, C=O×4).

$^1H$ NMR ($CDCl_3$): δ 1.16 (8H, bs, $CH_2$×4), 1.35 (18H, s, $CH_3$×6), 1.39 (18H, s, $CH_3$×6), 1.88 (1H, bs, CH), 2.38 (3H, s, $CH_3$ Tosyl), 3.10-3.12 (4H, bs, $NCH_2$×2), 3.19 (8H, bs, $NCH_2$×4), 3.93 (2H, t, J=7 Hz, $CH_2OTs$), 5.0 (1H, bs, NH), 5.08 (1H, bs, NH), 7.29 (2H, d, J=8 Hz, CH×2, Ar), 7.72 (2H, d, J=8 Hz CH×2, Ar)

IR (thin film) cm$^{-1}$: 3360, 2974, 2932, 2862, 1693, 1516, 1479, 1418, 1391, 1366, 1250, 1177, 1069, 959, 816, 775.

Mass Spec (Fabs) m/e : Calculated for $C_{40}H_{71}N_4O_{11}S$ (M+H) 815 Found 815

Step (g): (8-Azido-2-{[tert-butoxycarbonyl-(2-tert-carbonylamino-ethyl)-amino]-methyl}-octyl)-(2-tert-butyloxycarbonylamino-ethyl)-carbamic acid tert-butyl ester Toluene-4-sulfonic acid 8-[tert-butoxycarbonyl-(2-tert-butoxycarbonylaminoethyl-amino]-7-{[tert-butoxycarbonyl-(2-tert-butoxycarbonylaminoethyl)amino]methyl}-octyl ester (1.105 g, 1.36 mmol), sodium azide (350 mg, 5.4 mmol) and methanol (10 ml) were heated under reflux at 70-75° C. for 16 hours. After cooling, methanol was removed at room temperature under reduced pressure until about 1-2 ml remained. This residue was diluted with water (25 ml) and extracted with $CH_2Cl_2$ (25 ml×4). The organic extracts were combined, dried ($MgSO_4$), filtered and volatiles evaporated at room temperature (Note: Azides are potentially explosive and this step should be carried out behind a safety shield) to leave a pale yellow viscous residue which was the desired compound in a pure state. (Yield 820 mg, 88%).

$^{13}C$ NMR ($CDCl_3$): δ 26.3 ($CH_2$), 26.5 ($CH_2$), 28.3 ($CH_3$× 12), 28.7 ($CH_2$), 29.6 ($CH_2$), 29.8 ($CH_2$), 36.8 (broad, CH), 39.3 ($NCH_2$×2), 46.9 (Broad, $NCH_2$×2), 50.0 (broad, $NCH_2$× 2), 51.3 ($CH_2N_3$), 79.0 (OC×2), 79.8 (OC×2), 156.0 (C=O× 4).

$^1H$ NMR ($CDCl_3$): δ1.16 (8H, bs, $CH_2$×4), 1.29 (18H, s $CH_3$×6), 1.33 (18H, s, $CH_3$×6), 1.47 (2H, bt, J=6.5 Hz $CH_2$ adjacent CH), 1.86 (1H, bs, CH), 2.95-3.05 (4H, bs, $NCH_2$× 2), 3.05-3.20 (10H, bs, $NCH_2$×4 and $CH_2N_3$), 5.09 (2H, bs, NH×2)

IR (thin film) cm$^{-1}$: 3350, 2974, 2932, 2860, 2097 (Strong band $N_3$), 1694, 1520, 1470, 1418, 1391, 1366, 1250, 1167, 1069, 870, 777.

Step (h): (8-Amino-2-{[tert-butoxycarbonyl-(2-tert-carbonylamino-ethyl -amino]-methyl}-octyl)-(2-tert-butyloxycarbonylamino-ethyl-carbamic acid tert-butyl ester (Compound 2)

(8-Azido-2-{[tert-butoxycarbonyl-(2-tert-carbonylamino-ethyl)-amino]-methyl}-octyl)-(2-tert-butyloxycarbonylamino-ethyl)-carbamic acid tert-butyl ester (820 mg, 1.20 mmol), 10% palladium on charcoal (100 mg) and methanol (10 ml) were treated with hydrogen gas under a pressure of 30 atmospheres at room temperature for 16 hours. The solids were removed by filtration through Celite and the filter cake was washed with methanol (50 ml). Volatiles were removed from the filtrate to leave a viscous oil which was the desired material in a pure state. (Yield 700 mg, 89%).

$^3C$ NMR ($CDCl_3$): δ 26.4 ($CH_2$), 26.6 ($CH_2$), 28.4 ($CH_3$× 12), 32.9 ($CH_2$×2), 36.8 (broad, CH). 39.2 ($NCH_2$×2), 41.8 ($H_2NCH_2$), 46.9 (broad, $NCH_2$×2), 49.8 (broad, $NCH_2$×2), 78.9 (OC×2), 79.7 (OC×2), 156.0 (C=O×4).

$^1H$ NMR ($CDCl_3$): δ 1.08 (8H, bs, $CH_2$×4), 1.23 (18H, s, $CH_3$×6), 1.27 (20H, bs, $CH_3$×6 and $CH_2$), 1.77 (1H, bs, CH), 2.40 (2H, bs, $NH_2$), 2.50 (2H, t, J=7 Hz, $CH_2NH_2$), 2.97 (4H, bm, $NCH_2$×2), 3.00-3.16 (8H, bm, $NCH_2$×4), 5.21 (1H, bs, NH), 5.30 (1H, bs, NH).

IR (thin film) cm$^{-1}$: 3360, 1693, 1520, 1459, 1418, 1392, 1367, 1250, 1170, 1068, 964, 922, 871, 775, 733.

Mass Spec (Fabs) m/e: Calculated for $C_{33}H_{66}N_5O_8$ (M+H) 660 Found 660.

EXAMPLE 3

Synthesis of Compound 3

Step (a): Coupling of Compound 1 to benzylamine

Compound 1 (61.8 mg, 0.1 mmol), in $CH_2Cl_2$ (5 ml) was treated with benzylamine (10.7, mmol) diphenylphosphinic chloride (25.9 mg) and diisopropylamide (29 mg 0.22 mmol) in a (50 ml) round bottomed flask at 20° C. for 18 h. The reaction was then diluted with $CH_2Cl_2$ (20 ml) and washed with 1N hydrochloric acid (5 ml) and saturated aqueous potassium carbonate (5 ml). The $CH_2Cl_2$ layer was separated dried ($Na_2SO_4$) and concentrated in vacuo to a gum (~50 mg). The crude material was then chromatographed on silica in a gradient of ethyl acetate in petrol (100 ml each of 50%, 70%, and 90%). A small amount of the faster running impurity was collected followed closely by the main fraction.

$^1$H and $^{13}$C NMR spectra were run in $CDCl_3$. This indicated that the main fraction was the required pure compound.

Step (b): Deprotection of Boc Protecting Groups

The product from step (a) (27.8 mg, 0.039 mmol), in $CH_2Cl_2$ (0.5 ml) was treated with trifluoroacetic acid (0.5 ml) and the reaction allowed to stand at room temperature for 3 h. The reaction mixture was then concentrated in vacuo to a gum to remove excess acid and weighed (53 mg). $^1$H and $^{13}$C NMR ($CDCl_3$) indicated that the Boc groups had been completely removed. A weighed sample of Compound 2 was dissolved in water to give a 10 mmolar solution of the TFA salt, which was used for radiolabelling experiments.

EXAMPLE 4

Synthesis of Compound 6

Step (a): (8-Benzoylamino-2-{[tert-butoxycarbonyl-(2-tert-carbonylamino-ethyl)-amino]-methyl}-octyl)-(2-tert-butyloxycarbonylamino-ethyl)-carbamic acid tert-butyl ester Benzoic acid 2,5-dioxo-pyrrolidin-1-yl ester (20 mg, 0.091 mmol), in dry $CH_2Cl_2$ was added in one portion to a solution of Compound 2 (50 mg, 0.08 mmol) in $CH_2Cl_2$ (1 ml) and the solution stirred at room temperature for 16 hours. The reaction was diluted with $CH_2Cl_2$ (10 ml), extracted with water (15 ml×2), dried ($MgSO_4$), filtered and the solvent removed by rotary evaporation. The remaining residue was purified by chromatography on silica gel using with $CH_2Cl_2$/Methanol 94:6 ($r_f$=0.23) as eluent to give a colourless viscous oil. (Yield 25 mg, 41%).

$^{13}$C NMR ($CDCl_3$): δ 26.4 ($CH_2$), 26.8 ($CH_2$), 28.5 ($CH_3$× 12), 29.6 ($CH_2$×2), 29.7 ($CH_2$), 29.9 ($CH_2$), 36.6 (broad, CH), 39.4 ($NCH_2$×2), 40.0 (O=$CNCH_2$×2), 47.0 (broad, $NCH_2$× 2), 49.8 ($NCH_2$×2), 79.7 (O$C$×2), 80.0 (O$C$×2), 127.0 (Ar CH×2), 128.5 (ArCH×2), 131.3 (ArCH), 134.9 (ArC), 156.1 (C=O×4), 167.6 (Ar$C$=O).

$^1$H NMR ($CDCl_3$): δ 1.28 (8H, bs, $CH_2$×4), 1.38 (18H, s, $CH_3$×6), 1.42 (20H, bs, $CH_3$×6 and $CH_2$), 1.95 (1H, bs, CH), 3.1 (4H, bs, $NCH_2$×2) 3.22 (8H, bs, $NCH_2$×4), 3.42 (2H, bq, J=6 Hz, $CH_2$N-benzoyl), 5.08 (2H, bs, NH×2), 6.18 (1H, bs, HN-benzzoyl), 7.38-7.45 (3H, m, Ar CH×3), 7.74 (2H, bd, J=7 Hz, Ar CH×2), IR (thin film) cm$^{-1}$: 3350, 2976, 2932, 2859, 1693 (broad), 1652, 1520, 1419, 1391, 1367, 1251, 1166, 732

Mass Spec (Fabs) m/e : Calculated for $C_{40}H_{70}N_5O_9$ (M+H) 764 Found 764.

Step (b): Deprotection of Boc Protecting Groups

The Boc tetraamine benzamide from step (a) (42 mg, 0.056 mmol), in $CH_2Cl_2$ (0.5 ml) was treated with trifluoroacetic acid (0.5 ml) and the reaction allowed to stand at room temperature for 3 h. The reaction was then concentrated in vacuo to remove excess acid, giving a gum. Expected weight (45 mg), found weight (45.7 mg). $^1$H and $^{13}$C NMR ($CD_3OD$) indicated that the Boc groups had been completely removed and that it contained the required compound. A weighed sample of the compound was dissolved in water to give a 10 mmolar solution of the TFA salt (56 μmol in 5.6 ml) which was used for radiolabelling.

EXAMPLE 5

Synthesis of Compound 4

All reactions were carried out in a manual nitrogen bubbler apparatus.

Step (a): Attachment of Losartan to Trityl Derivatised Solid Support

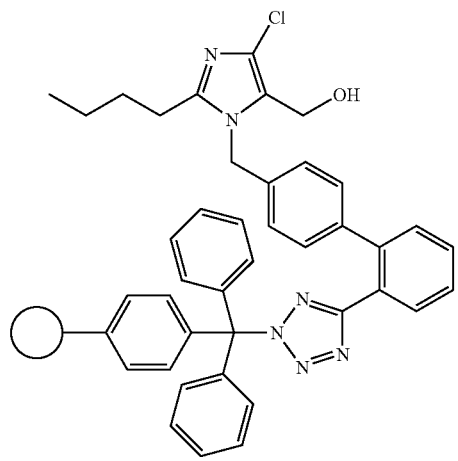

Losartan (MSD, 0.236 g, 0.558 mmol) and triethylamine (Fluka, 0.233 ml, 1.67 mmol) were added to a suspension of trityl chloride resin (Novabiochem, susbstitution 1.24 mmol/ g, 0.300 g) in DMF (5 ml). After 4 days the resin was drained and washed. An aliquot of the resin was cleaved (dichloromethane/ TFA/ triisopropylsilane, 92.5:5.0:2.5, 15 min). HPLC analysis (column Phenomenex Luna C18(2) 3 μm 4.6×50 mm, solvents: A=water/0.1% TFA and B=acetonitrile/0.1% TFA; gradient 10-40% B over 10 min; flow 2.0 mmin, UV detection at 214 and 254 nm) gave a peak with $t_R$ 6.7 minutes corresponding to losartan. The resin was treated with dichloromethane/ methanol/diisopropylethylamine solution (17:2:1, 20 ml, 1 h), washed with dichloromethane and dried.

Step (b): Replacement of the Hydroxyl Group by Azide

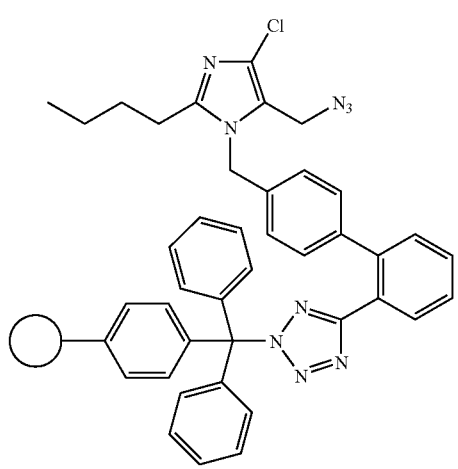

Diphenylphosphoryl azide (Aldrich, 0.481 ml, 2.23 mmol) and DBU (0.611 ml, 4.09 mmol) were added to a suspension of resin bound losartan from step (a) (0.372 mmol) in THF (10 ml). The reaction was left overnight. An aliquot of the resin was cleaved as described for step (a). Analysis by LC-MS (column Phenomenex Luna C18(2) 3 µm 50×4.60 mm, solvents: A=water/0.1% TFA and B=acetonitrile/0.1% TFA; gradient 20-80% B over 10 min; flow 1 ml/min, UV detection at 214 nm, ESI-MS) gave a peak, $t_R$ 7.3 minutes, with m/z 448.1 (MH$^+$) corresponding to the structure.

Step (c) Reduction of the Azide Group to Amine

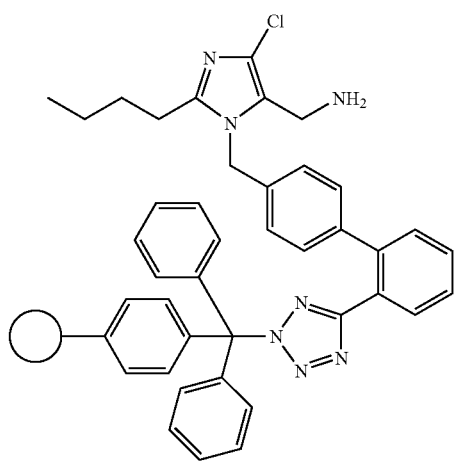

To a suspension of the resin from step (b) in THF (4 ml) was added tin(II)chloride (Acros, 0.141 g, 0.744 mmol), thiophenol (Fluka, 0.304 ml, 2.976 mmol) and triethylamine (Fluka, 0.311 ml, 2.23 mmol). After 1.5 hour an aliquot of the resin was cleaved as described under a). LC-MS analysis (column Phenomenex Luna C18(2) 3 µm 50×4.60 mm, solvents: A=water/0.1% TFA and B=acetonitrile/0.1% TFA; gradient 20-80% B over 10 min; flow 1 ml/min, UV detection at 214 nm, ESI-MS) gave a peak at 1.9 minutes with m/z 422.2 (MH$^+$) as expected for amine.

Step (d): Losartan-Leu-Tetraamine Chelator (Compound 4)

Fmoc-Leu-OH (Novabiochem, 0.030 g, 0.084 mmol) was coupled to an aliquot of the resin bound amino-losartan from step (c) (0.042 mmol) in DMF using standard coupling reagents (HATU and DIEA) and standard Fmoc-cleavage protocol (20% piperidine in DMF). Completion of coupling was checked by standard Kaiser test. To the resin was then coupled Compound 1 (0.026 g, 0.042 mmol) using the same coupling reagents (HATU and DIEA) in DMF. After four hours the product was cleaved off the resin and the Boc groups were removed in the same step (dichloromethane/TFA/triisopropylsilane, 47.5:50:2.5 solution for one hour). The solution was filtered, concentrated and purified by preparative HPLC (column Phenomenex Luna C18(2) 5 µm 21.2×250 mm, solvents: A=water/0.1% TFA and B=acetonitrile/0.1% TFA; gradient 20-40% B over 60 min; flow 10.0 ml/min, UV detection at 214 nm) to give 5 mg of product after lyophilisation. LC-MS analysis (column Phenomenex Luna C18(2) 3 µm 50×4.60 mm, solvents: A=water/0.1% TFA and B=acetonitrile/0.1% TFA; gradient 10-80% B over 10 min; flow 0.3 ml/min, UV detection at 214 and 254 nm, ESI-MS) $t_R$ 5.1 minutes, m/z 735.4 (MH$^+$)) confirmed the structure.

EXAMPLE 6

Synthesis of Compound 5

The compound was synthesised on solid support as described in Example 4. Fmoc-Leu-OH (Novabiochem, 0.033 g, 0.092 mmol) and Fmoc-amino PEG diglycolic acid (Polypure, 0.049 mg, 0.092 mmol) were successively coupled to an aliquot of the resin bound amino-losartan from Example 4(c) (0.046 mmol) in DMF using standard coupling reagents (HATU and DIEA) and standard Fmoc-cleavage protocol (20% piperidine in DMF). Completion of coupling was checked by standard Kaiser test. To the resin was then coupled Compound 1 (0.029 g, 0.046 mmol) using the same coupling reagents (HATU and DIEA) in DMF. The reaction was left overnight, then the product was cleaved off the resin and the Boc groups were removed in the same step (dichloromethane/TFA/ triisopropylsilane, 47.5:50:2.5 solution for one hour). The solution was filtered, concentrated and purified by preparative HPLC (column Phenomenex Luna C18(2) 5 µm 21.2×250 mm, solvents: A=water/0.1% HCOOH and B=acetonitrile/0.1% HCOOH; gradient 10-40% B over 60 min; flow 10.0 ml/min, UV detection at 214 nm) to give 3.5 mg of product after lyophilisation. LC-MS analysis (column Phenomenex Luna C18(2) 3 µm 50×4.60 mm, solvents: A=water/0.1% HCOOH and B=acetonitrile/0.1% HCOOH; gradient 10-40% B over 10 min; flow 0.3 ml/min, V detection at 214 and 254 nm, ESI-MS) $t_R$ 4.7 minutes, m/z 1025.4 (MH$^+$)) confirmed the structure.

EXAMPLE 7

Synthesis of Compound 8

Step (a): Synthesis of N-Boc-N-[FmocNH-CH$_2$CH$_2$]-Gly-OH 1 g of N-[FmocNH—CH$_2$CH$_2$]-Gly-OtBu.HCl (Fluka 09660) was treated with 20 mL of 50% trifluoroacetic acid (TFA) in dichloromethane containing 0.5 mL of triisopropylsilane for 60 min. The mixture was evaporated in vacuo and the residue redissolved in 20 mL of 50% tetrahydrofuran in water. 2.6 g of tert-butyloxycarbonyl anhydride and 1.2 mL of N-methylmorpholine were added and the mixture stirred for four days. Tetrahydrofuran was then evaporated in vacuo and the residue redissolved in dichloromethane. The organic layer was washed with water and dried with $MgSO_4$. Dichloromethane was evaporated in vacuo and the residue redissolved in 5 mL of dimethylformamide. The dimethylformamide solution was diluted with 400 mL of 60% acetonitrile in water and pumped onto a preparative RP-HPLC column for purification (30-80% B over 40 min, where $A=H_2O$/0.1% TFA and $B=CH_3CN$/0.1% TFA, at a flow rate of 50 mL/min on a Phenomenex Luna 10μ C18 (2) 250×50 mm column) affording 450 mg pure product. The product was analysed by analytical HPLC (gradient, 20-70% B over 10 min where $A=H_2O$/0.1% TFA and $B=CH_3CN$/0.1% TFA; flow, 0.3 mL/min; column, Phenomenex Luna 3μ C18 (2) 50×2 mm; detection, UV 214 nm; product retention time 8.66 min). Further product characterisation was carried out using electrospray mass spectrometry ($MH^+$ calculated, 441.2; $MH^+$ found, 440.8).

Step (b): Synthesis of N—(($CH_2$)—$NHCOCH_2$-tetraamine)-Gly-Arg-Val-Tyr-Ile-His-Pro-Ile-OH (Compound 8)

A peptide analogue of Angiotensin II was synthesised on an Applied Biosystems 433 A peptide synthesizer starting with 0.1 mmol Fmoc-Ile-Wang resin. An excess of 1 mmol pre-activated amino acids [using O-Benzotriazol-1-yl-N,N,N',N'-tetramethyluronium hexafluorophosphate (HBTU)] was applied in the coupling steps up to Arginine. 123 mg of N-Boc-N-[FmocNH—$CH_2CH_2$]-Gly-OH, 114 mg of N-[(dimethylamino)-1H-1,2,3triazolo-[4,5-b]pyridin-1-ylmethylene]-N-methylmethanaminium hexafluorophosphate N-oxide (HATU) and 60 μL of N-methylmorpholine were dissolved in dimethylformamide and stirred for 5 min, then added to the resin in a nitrogen bubbler apparatus. The reagents were removed after 2 hrs and the resin washed with dimethylformamide and dichloromethane. The resin was treated with 20 % piperidine in dimethylformamide (3×10 ml) and washed with dimethylformamide. 23 mg of Compound 1, 14 mg of HATU and 7.5 μL of N-methylmorpholine were dissolved in dimethylformamide for 10 min and added to the resin. The reagents were removed after 4 hrs and the resin washed with dimethylformamide and dichloromethane. The simultaneous removal of side-chain protecting groups and cleavage of the peptide from the resin was carried out in 10 mL of trifluoroacetic acid containing 2.5% triisopropylsilane and 2.5% water for 90 minutes. Trifluoroacetic acid was removed in vacuo, diethyl ether added to the residue and the precipitated product washed with diethyl ether and air-dried.

Purification by preparative RP-HPLC (0-30% B over 40 min, where $A=H_2O$/0.1% TFA and $B=CH_3CN$/0.1% TFA, at a flow rate of 10 mL/min on a Phenomenex Luna 10μ C18 (2) 250×21.20 mm colunm) of the product afforded 32 mg pure chelate-peptide conjugate. The product was analysed by analytical HPLC (gradient, 5-50% B over 20 min where $A=H_2O$/0.1% TFA and $B=CH_3CN$/0.1% TFA; flow, 1 mL/min; column, Phenomenex Luna 3μ C18 (2) 50×2 mm; detection, UV 214 nm; product retention time 5.22 min). Further product characterisation was carried out using electrospray mass spectrometry ($MH^+$ calculated, 1197.8; $MH^+$ found, 1197.8).

EXAMPLE 8

$^{99m}$Tc Radiolabelling of Compounds 3 to 7

A lyophilised kit ("Chelakit A plus") containing the following ingredients was prepared:

| Component | M. Wt. | mg |
|---|---|---|
| $SnCl_2·2H_2O$ | 225.63 | 0.016 |
| $MDP(H_4)$ | 176.00 | 0.025 |
| $NaHCO_3$ | 84.01 | 4.5 |
| $Na_2CO_3$ | 105.99 | 0.6 |
| NaPABA | 159.12 | 0.200 |

25-50 μg of the compound to be labelled (dissolved in 25-50 μL solvent) was added to CHELAKIT-A plus, followed by generator eluate ($^{99m}TcO_4^-$ in saline, 1.0 mL). The solution was mixed and left at room temperature for 20-30 minutes.

Compounds 3 and 6 label technetium at room temperature at a pH of 9 to give the corresponding cationic $^{99m}$Tc complexes in high yield (RCP>90%). The tetraamine complexes were purified by HPLC (mobile phase: 0.1% TFA in water, 0.1% TFA in acetonitrile; XTERRA $RP_{18}$ 3.5 μm 4.6×150 mm column) and are stable in 50 mM phosphate buffer at 37° C. for 2 hours (RCP>95% by HPLC after 2 hours).

EXAMPLE 9

Measurement of Lipophilicity (LogP) of the $^{99m}$Tc Complexes

The octanol-water partition coefficients (LogP) of the $^{99m}$Tc complexes of Example 8 were determined as follows:

10 μL of the HPLC-purified $^{99m}$Tc complex from Example 8 was mixed with 1-octanol (2 ml) and 50 mM phosphate buffer (pH=7.4, 2.0 ml) in a centrifuge tube. The tube was vortexed at room temperature for 1 min and then was centrifuged at high speed for 60 min. 0.1 ml samples of both phases were pipetted into other test tubes with adequate care to avoid cross contamination between the phases, and were counted in a Wallac Wizzard gamma-counter. The measurement was repeated three times.

The partition coefficient, P, was calculated as follows:

$P = (cpm$ in octanol$-(cpm$ background$))/((cpm$ in water$-(cpm$ background$))$.

Usually the final partition coefficient value was expressed as log P.

The results are given in Table 1:

TABLE 1

Log P values of the technetium complexes tetra-amine compounds

| $^{99m}$Tc Complex of Compound Number | Log P (octanol/50 mM phosphate buffer) |
|---|---|
| 3 | <−2 |
| 4 | +0.6 |
| 5 | −0.1 |
| 6 | −1.8 |
| 7 | <−2 |

EXAMPLE 10

Biodistribution of the $^{99m}$Tc Complexes

The $^{99m}$Tc complexes of Compounds 4, 5 and 7 were prepared as described in Example 8. Experiments were performed at two predetermined time points (2 and 120 minutes) post injection (p.i.) of the Test Item in normal male Wistar rats (180 to 220 g). Animals were anaesthetised with Halothane (6% in oxygen), injected with 0.1 ml (500 MBq/ml) Test Item, sacrificed, dissected and the samples assayed for radioactivity. The results are given in Table 1:

TABLE 1

Biodistribution of the $^{99m}$Tc Complexes

| % ID/G | Compound 4 | Compound 5 | Compound 7 |
|---|---|---|---|
| Blood 5 min | 3.26 | 1.5 | 0.84 |
| Blood 120 min | 0.91 | 0.26 | 0.05 |
| Muscle 120 min | 0.34 | 0.9 | 0.1 |
| Liver 120 min | 6.52 | 3.53 | 1.55 |
| Lung 120 min | 1.84 | 0.6 | 0.4 |
| Heart 120 min | 0.44 | 0.13 | 0.1 |
| Heart/blood | 0.49 | 0.5 | 2 |
| Heart/lung | 0.24 | 0.21 | 0.25 |
| Heart/liver | 0.07 | 0.04 | 0.06 |
| Heart/muscle | 1.3 | 1.44 | 1 |
| % retained over 2 h Clearance (% ID) | | | |
| Urine (K, B, U)120 min | 21.13 | 14.45 | 64.26 |
| HBS 120 min | 74.65 | 54.21 | 19.63 |
| Log P | 0.6 | −0.1 | <−2 |

EXAMPLE 11

Alternative Preparation of Compound 1

N,N'-Bis(2-tert-butoxycarbonylamino-ethyl)-2-(2-hydroxyethyl)-1,3-di(tert-butoxycarbonylamino)propane from Example 1 step (e) was dissolved in carbon tetrachloride (14 ml) and acetonitrile (14 ml). Water (21 ml) was added to give a biphasic mixture followed by sodium periodate (4.5 g, 21 mmol) and ruthenium chloride hydrate (35 mg, 0.026 mmol). The resulting dark brown solution was stirred at room temperature for 1 hour and then diluted with $CH_2Cl_2$ (40 ml). The organic layer was separated and the aqueous phase extracted with more $CH_2Cl_2$ (40 ml×3). All the organic extracts were combined, dried ($MgSO_4$), filtered and volatiles evaporated under reduced pressure to leave the sodium salt of Compound 1 as a dark viscous residue which was used without further purification (4.15 g, 96%).

$^{13}$C NMR (CDCl$_3$) : $\delta_C$ 28.2 (×12)(CH$_3$), 34.1 (CH$_2$), 34.4 (CH), 38.6 (×2)(NCH$_2$), 46.8 (×2)(NCH$_2$), 49.3 (×2)(NCH$_2$), 79.0 (×2)(OC), 80.2 (×2)(OC), 155.9 (×4)(C=O), 175.4 (COOH).

$^1$H NMR (CDCl$_3$): $\delta_H$ 1.29 (18H, s, CH$_3$×6), 1.35 (18H, s, CH$_3$×6), 2.19 (1H, br, CH), 2.40 (2H, br, CH$_2$), 3.05-3.23 (12H, br, NCH$_2$×6), 5.10-5.24 (2H, br, NH×2)

Mass Spec (ESI) m/e: Calculated for (M+Na) C$_{29}$H$_{54}$O$_{10}$N$_4$Na 641.3738, Found 641.3787

EXAMPLE 12

Preparation of Compound 9

1,3-Dicyclohexylcarbodiimide (DCC; 2.16 g, 10.5 mmol) was added in one portion to a stirred solution of Compound 1 (4.15 g, 6.90 mmol) and N-hydroxysuccinimide (1.81 g, 15.7 mmol) in dry THF (30 ml). The mixture was stirred at room temperature for 16 hours and then precipitated DCU (1,3-dicyclohexylurea) was removed by filtration. Volatiles were evaporated from the filtrate leaving a waxy residue to which dry ether (50 ml) was added precipitating more DCU which was removed by filtration. The ethereal solution was washed with water (25 ml×2), dried (MgSO$_4$), filtered and solvent evaporated under reduced pressure to leave a waxy solid. This solid was purified by chromatography on silica gel eluting with a CH$_2$Cl$_2$/ether mixture (1:1) until unreacted DCC was removed. The eluent was changed to Ether and the required product (r$_f$=0.4, DCM/Et$_2$O 1:1) was isolated as a colourless solid (2.7 g, 57%) m p 66-68° C.

$^{13}$C NMR (CDCl$_3$): $\delta_C$ 25.6 (×2)(CH$_2$), 28.4 (×12)(CH$_3$), 31.8 (CH$_2$), 35.2 (CH), 39.3 (×2)(NCH$_2$), 47.1 (×2)(NCH$_2$), 49.1 (×2)(NCH$_2$), 79.9 (×2)(OC), 80.5 (×2)(OC), 156.1 (×4)(C=O), 167.7 (C=O), 169.1 (×2)(C=O).

$^1$H NMR (CDCl$_3$) : $\delta_H$ 1.35 (18H, s, CH$_3$×6), 1.41 (18H, s, CH$_3$×6), 2.52 (3H, brs, CH & CH$_2$), 2.77 (4H, s, CH$_2$×2), 3.10-3.35 (12H, brs, NCH$_2$×6), 5.08 (2H, brsNH×2)

Mass Spec (ESI) m/e: Calculated for (M+Na) C$_{33}$H$_{54}$N$_5$O$_{12}$Na 738.3896, Found 738.3893

What is claimed is:

1. A technetium complex of Formula (I):

where:
X is —NR—, —CO$_2$—, —CO—, —NR(C=S)—, —NR(C=O)—, —CONR— or a Q group;
each Y is independently a D- or L-amino acid, —CH$_2$—, —CH$_2$OCH$_2$— or —OCH$_2$CH$_2$O— or an X group;
Z is a synthetic biological targeting moiety;
n is an integer of value 1 to 8;
m is an integer of value 0 to 30;
R is H, C$_{1-4}$ alkyl, C$_{2-4}$ alkoxyalkyl, C$_{1-4}$ hydroxyalkyl, or C$_{1-4}$ fluoroalkyl;
Q is A is a counterion;
with the proviso that the X—(Y)$_m$ chain of atoms lacks bonds in which one heteroatom is directly bonded to another.

2. The technetium complex of claim 1, where the technetium radioisotope is $^{99m}$Tc or $^{94m}$Tc.

3. The technetium complex of claim 1, where n is 1 to 6 and X is —CONR— or —NR(C=O)—.

4. The technetium complex of claim 3, where X is —CONH— or —NH(C=O)—.

5. The technetium complex of claim 1, where —(Y)$_m$— comprises a PEG group of formula (—OCH$_2$CH$_2$O—)$_w$ where w is an integer of value 3 to 25.

6. The technetium complex of claim 5, where w is 6 to 22.

7. The technetium complex of claim 1, where —(Y)$_m$— comprises 1 to 10 amino acids.

8. The technetium complex of claim 7, where the amino acids are independently chosen from glycine, lysine, aspartic acid, glutamic acid or serine.

9. The technetium complex of claim 1, where Z is chosen from:
   (i) a 3-30 mer peptide;
   (ii) an enzyme substrate, enzyme antagonist or enzyme inhibitor.

10. A chelator conjugate useful in the preparation of the technetium complexes of claim 1, said conjugate being of Formula II:

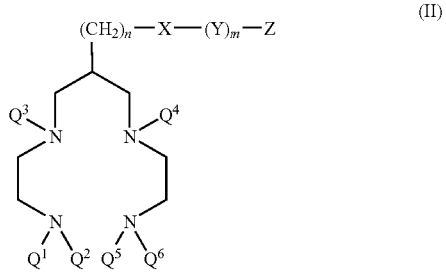

(II)

where: X, Y, Z, n and m are as defined in claim 1;
Q$^1$ to Q$^6$ are independently Q groups, where Q is H or an amine protecting group.

11. The chelator conjugate of claim 10, where each of Q$^1$ to Q$^6$ is H.

12. The chelator conjugate of claim 10, where Q$^1$ and Q$^6$ are both H, and Q$^2$, Q$^3$, Q$^4$ and Q$^5$ are each tert-butoxycarbonyl.

13. A radiopharmaceutical which comprises the technetium complex of Formula I of claim 1, wherein A is a pharmaceutically acceptable counterion, together with a biocompatible carrier in a form suitable for human administration.

14. The radiopharmaceutical of claim 13, where the technetium radioisotope is $^{99m}$Tc or $^{94m}$Tc.

15. A kit for the preparation of the radiopharmaceutical, which comprises the technetium complex of Formula I, wherein A is a pharmaceutically acceptable counterion, together with a biocompatible carrier in a form suitable for human administration comprising:
   (i) the chelator conjugate of claim 10;
   (ii) a biocompatible reducing agent.

16. The kit of claim 15, where the biocompatible reducing agent comprises stannous ion.

17. The kit of claim 15, where each of Q$^1$ to Q$^6$ is H.

18. The kit of claim 15, where Z is chosen from:
   (i) a 3-30 mer peptide;
   (ii) an enzyme substrate, enzyme antagonist or enzyme inhibitor.

19. A compound of Formula III:

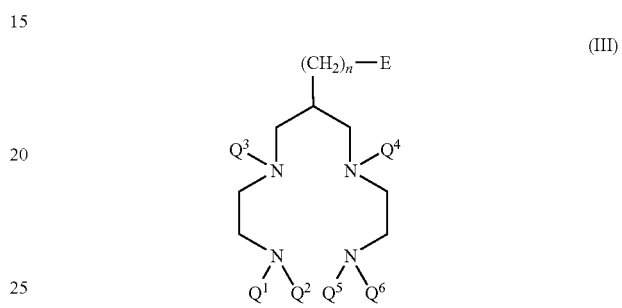

(III)

where: Q$^1$ to Q$^6$ are independently groups where Q is H or an amine protecting group;
n is an integer of value 1 to 8;
E is a functional group suitable for conjugation to the biological targeting moiety (Z) of claim 1, wherein E is chosen from —NH$_2$, —CO$_2$M, —NCS, —NCO, maleimide or acrylamide,
where: M is H, a cation, a protecting group or an active ester;
with the proviso that:
when n=3, then at least one of Q$^1$ to Q$^6$ is an amine protecting group.

20. The compound of claim 19, where E is —NH$_2$ or —CO$_2$M.

21. The compound of claim 19, where n is 1 to 6.

* * * * *